US010736510B2

(12) United States Patent
Cronin

(10) Patent No.: US 10,736,510 B2
(45) Date of Patent: Aug. 11, 2020

(54) MEDICAL BRACELET STANDARD

(71) Applicant: KONINKLIJKE PHILIPS N.V., Eindhoven (NL)

(72) Inventor: John Cronin, Bonita Springs, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 24 days.

(21) Appl. No.: 15/537,473

(22) PCT Filed: Dec. 14, 2015

(86) PCT No.: PCT/EP2015/079516
§ 371 (c)(1),
(2) Date: Jun. 19, 2017

(87) PCT Pub. No.: WO2016/096678
PCT Pub. Date: Jun. 23, 2016

(65) Prior Publication Data
US 2018/0000346 A1    Jan. 4, 2018

Related U.S. Application Data

(60) Provisional application No. 62/094,871, filed on Dec. 19, 2014.

(30) Foreign Application Priority Data

Jun. 5, 2015   (EP) .................................... 15170855

(51) Int. Cl.
*A61B 5/00*    (2006.01)
*G06F 19/00*   (2018.01)
(Continued)

(52) U.S. Cl.
CPC .............. *A61B 5/0022* (2013.01); *A61B 5/00* (2013.01); *A61B 5/0205* (2013.01);
(Continued)

(58) Field of Classification Search
CPC ....... A61B 5/00; A61B 5/0022; A61B 5/0205; A61B 5/6801; A61B 5/6898; G06F 19/00;
(Continued)

(56) References Cited

U.S. PATENT DOCUMENTS 3,634,885 A * 1/1972 Barkley .................... A61B 5/00
340/573.1
6,561,975 B1 * 5/2003 Pool ...................... A61B 5/0031
600/300

(Continued)

FOREIGN PATENT DOCUMENTS

CA          2213997 A1 *  9/1996  ............. G16H 10/60
CN      104167079 A      11/2014
(Continued)

*Primary Examiner* — Carl H Layno
*Assistant Examiner* — Michael J Lau

(57) ABSTRACT

Various embodiments described herein relate to a wearable device for monitoring health parameters of a patient. According to various embodiments, a wearable device, associated mobile device, or other user device may receive health parameters of the user obtained by at least one sensor configured to sense one or more health parameters from the user; receive an identification of a medical alert to be provided to third parties with respect to the user, persist the identification of the medical alert in a memory of the user device, and repeatedly transmit at least one of the identification of the medical alert and an indication of the availability of the medical alert via a communications interface of the user device configured to communicate wirelessly with nearby reader devices.

12 Claims, 10 Drawing Sheets

(51) Int. Cl.
*G16H 40/63* (2018.01)
*G08B 21/04* (2006.01)
*G08B 25/14* (2006.01)
*A61B 5/0205* (2006.01)
*G16H 10/60* (2018.01)
*G16H 15/00* (2018.01)

(52) U.S. Cl.
CPC .......... *A61B 5/6801* (2013.01); *A61B 5/6898* (2013.01); *G06F 19/3418* (2013.01); *G08B 21/0453* (2013.01); *G08B 25/14* (2013.01); *G16H 40/63* (2018.01); *G16H 10/60* (2018.01); *G16H 15/00* (2018.01)

(58) Field of Classification Search
CPC .... G06F 19/3418; G08B 25/14; G16H 40/64; G16H 40/10; G16H 40/60; G16H 15/00
USPC ............... 600/301; 607/32, 60; 128/903; 340/539.12
See application file for complete search history.

(56) References Cited

U.S. PATENT DOCUMENTS

| | | | | |
|---|---|---|---|---|
| 7,120,488 | B2* | 10/2006 | Nova | A61N 1/37258 607/2 |
| 8,560,968 | B1* | 10/2013 | Nair | G16H 40/63 715/839 |
| 2004/0006492 | A1* | 1/2004 | Watanabe | A61B 5/0002 705/2 |
| 2005/0115561 | A1* | 6/2005 | Stahmann | A61B 5/0031 128/200.24 |
| 2005/0192487 | A1* | 9/2005 | Cosentino | A61B 5/0002 600/300 |
| 2006/0049936 | A1* | 3/2006 | Collins, Jr. | A61B 5/1115 340/539.11 |
| 2006/0136015 | A1* | 6/2006 | Park | A61B 5/0031 607/60 |
| 2007/0197878 | A1* | 8/2007 | Shklarski | A61B 5/02055 600/300 |
| 2007/0273504 | A1* | 11/2007 | Tran | A61B 5/0022 340/539.12 |
| 2007/0294113 | A1* | 12/2007 | Settimi | G06Q 50/24 705/3 |
| 2008/0114574 | A1* | 5/2008 | Chen | G16H 50/20 703/2 |
| 2008/0129518 | A1* | 6/2008 | Carlton-Foss | A61B 5/1117 340/573.1 |
| 2008/0146906 | A1* | 6/2008 | Baker | A61B 5/0059 600/407 |
| 2008/0294020 | A1* | 11/2008 | Sapounas | A61B 5/0024 600/301 |
| 2008/0294457 | A1* | 11/2008 | Cordery | G06F 19/328 705/2 |
| 2010/0076321 | A1* | 3/2010 | Zhang | A61B 5/0205 600/483 |
| 2010/0094110 | A1* | 4/2010 | Heller | A61B 5/14532 600/345 |
| 2010/0120374 | A1* | 5/2010 | Imai | A61B 5/0002 455/68 |
| 2010/0285771 | A1* | 11/2010 | Peabody | G08B 25/016 455/404.2 |
| 2010/0312188 | A1 | 12/2010 | Robertson et al. | |
| 2011/0140896 | A1* | 6/2011 | Menzel | A61B 5/02055 340/573.1 |
| 2011/0173308 | A1* | 7/2011 | Gutekunst | G06F 19/3418 709/222 |
| 2011/0320130 | A1* | 12/2011 | Valdes | G06F 19/3418 702/19 |
| 2012/0041278 | A1* | 2/2012 | Sadhu | G08B 21/0453 600/301 |
| 2012/0206262 | A1 | 8/2012 | Grasso | |
| 2013/0006064 | A1* | 1/2013 | Reiner | A61B 5/0022 600/300 |
| 2014/0088392 | A1* | 3/2014 | Bernstein | G06F 19/3418 600/365 |
| 2014/0118138 | A1* | 5/2014 | Cobelli | A61B 5/0022 340/539.12 |
| 2014/0249858 | A1* | 9/2014 | Moore | G16H 10/60 705/3 |
| 2014/0266787 | A1* | 9/2014 | Tran | A61B 5/0022 340/870.07 |
| 2014/0316792 | A1* | 10/2014 | Siddiqui | G06F 19/3418 705/2 |
| 2014/0343371 | A1* | 11/2014 | Sowers, II | A61B 5/1455 600/301 |
| 2014/0358585 | A1* | 12/2014 | Reiner | G06F 16/219 705/3 |
| 2015/0257654 | A1* | 9/2015 | Bennett-Guerrero | A61B 5/1121 600/301 |
| 2015/0289820 | A1* | 10/2015 | Miller | A61B 5/7221 600/300 |
| 2016/0324478 | A1* | 11/2016 | Goldstein | A61B 5/721 |
| 2017/0273622 | A1* | 9/2017 | Boesen | G08B 25/016 |

FOREIGN PATENT DOCUMENTS

JP 2008029590 A * 2/2008
JP 2008029590 A 2/2008

* cited by examiner

MEDICAL BRACELET STANDARD

CROSS-REFERENCE TO PRIOR APPLICATIONS

This application is the U.S. National Phase application under 35 U.S.C. § 371 of International Application No. PCT/EP2015/079516, filed on Dec. 14, 2015, which claims the benefit of European Application No. 15170855.9, filed Jun. 5, 2015 and U.S. Provisional Application Ser. No. 62/094,871 filed Dec. 19, 2014. These applications are hereby incorporated by reference herein, for all purposes.

TECHNICAL FIELD

Various embodiments described herein generally relate to wearable technology. More specifically, but not exclusively, the present invention relates to medical bracelet standards.

BACKGROUND

Wearable electronic devices, or as used herein, wearable technology is a new class of electronic systems that can provide data acquisition through a variety of unobtrusive sensors that may be worn by a user. The sensors gather information, for example, about the environment, the user's activity, or the user's health status. However, there are significant challenges related to the coordination, computation, communication, privacy, security, and presentation of the collected data. Additionally, there are challenges related to power management given the current state of battery technology. Furthermore, analysis of the data is needed to make the data gathered by the sensors useful and relevant to end-users. In some cases, additional sources of information may be used to supplement the data gathered by the sensors. The many challenges that wearable technology presents require new designs in hardware and software.

Wearable technology may include any type of mobile electronic device that can be worn on the body, attached to or embedded in clothes and accessories of an individual, and currently existing in the consumer marketplace. Processors and sensors associated with the wearable technology can display, process or gather information. Such wearable technology has been used in a variety of areas, including monitoring health of the user as well as collecting other types of data and statistics. These types of devices may be readily available to the public and may be easily purchased by consumers. Examples of some wearable technology in the health arena include FITBIT, NIKE+ FUELBAND, and the APPLE WATCH devices.

Medical bracelets are devices that generally include information about an individual's medical conditions and emergency contact information. These bracelets are helpful in providing information to others (e.g., instructions for care, emergency contacts) in situations where the individual is unable to communicate for help or incapacitated.

SUMMARY

Various embodiments described herein relate to a user device including: a communications interface configured to communicate wirelessly with nearby reader devices; a memory; and a processor in communication with the communications interface and the memory, wherein the processor is configured to: receive health parameters of the user obtained by at least one sensor configured to sense one or more health parameters from the user, receive an identification of a medical alert to be provided to third parties with respect to the user, persist the identification of the medical alert in the memory, and repeatedly transmit, via the communications interface, at least one of the identification of the medical alert and an indication of the availability of the medical alert.

Various embodiments described herein relate to a method performed by a user device for providing medical alert information, the method including: receiving, by a processor of the user device, health parameters of the user obtained by at least one sensor configured to sense one or more health parameters from the user; receiving an identification of a medical alert to be provided to third parties with respect to the user, persisting the identification of the medical alert in a memory of the user device, and repeatedly transmitting at least one of the identification of the medical alert and an indication of the availability of the medical alert via a communications interface of the user device configured to communicate wirelessly with nearby reader devices.

Various embodiments described herein relate to a non-transitory machine-readable storage medium encoded with instructions for execution by a user device for providing medical alert information, the non-transitory machine-readable storage medium including: instructions for receiving, by a processor of the user device, health parameters of the user obtained by at least one sensor configured to sense one or more health parameters from the user; instructions for receiving an identification of a medical alert to be provided to third parties with respect to the user, instructions for persisting the identification of the medical alert in a memory of the user device; and instructions for repeatedly transmitting at least one of the identification of the medical alert and an indication of the availability of the medical alert via a communications interface of the user device configured to communicate wirelessly with nearby reader devices.

Various embodiments additionally include the sensor, wherein the user device is configured to be attached to the user.

Various embodiments are described wherein, in transmitting the identification of the at least one medical alert, the processor is further configured to additionally transmit at least one of the health parameters with the medical alert.

Various embodiments are described wherein the processor is further configured to select the at least one of the health parameters for transmission based on the identification of the medical alert.

Various embodiments are described wherein, in receiving the identification of a medical alert, the processor is configured to receive a user selection of the medical alert from a list of predefined possible medical alerts.

Various embodiments are described wherein the processor is further configured to: identify the occurrence of a medical event based on the received health parameters, and begin the repeated transmission in response to the identification of the occurrence of the medical event.

Various embodiments are described wherein, in identifying the occurrence of a medical event, the processor is configured to: identify a trigger associated with the medical event based on the received identification of the medical alert, determine that the trigger is applicable based on comparing the trigger to the received health parameters, and identify the occurrence of the medical event based on determining that the trigger is applicable, whereby the processor monitors for occurrence of the medical event in response to receiving the identification of the medical alert.

Various embodiments described herein relate to systems for health monitoring. Such systems may include a wearable device for a user and one or more devices associated with evaluating entities. The wearable device may include memory that stores user information including medical information pertaining to a medical condition of the user to be monitored, one or more sensors that monitor one or more physical parameters of the user, a processor that executes instructions to measure one or more physical parameters of the user and to evaluate a medical condition of the user based on the measured physical parameters and the medical information pertaining to the user medical condition to be monitored that is stored in memory, and a communication interface that transmits the evaluation over a wireless communication network to the devices of the one or more evaluating entities. Such evaluation may include the measured physical parameters, wherein the one or more evaluating entities can use the transmitted evaluation to further evaluate the detected medical condition.

Further embodiments may include methods for health monitoring. Such methods may include storing user information in memory of a user device pertaining to a user medical condition to be monitored, monitoring one or more physical parameters of a user where the one or more physical parameters correspond to the monitored medical condition and are measured by one or more sensors of the user device, executing instructions to measure one or more physical parameters of the user and to evaluate a medical condition of the user based on the measured physical parameters of the user and the information pertaining to the user medical condition to be monitored stored in memory, and transmitting the evaluation over a wireless communication network to one or more evaluating entities. Such evaluation may include the measured physical parameters for further evaluation of the detected medical condition. Additional embodiments may relate to a non-transitory computer-readable storage media, having embodied thereon a computer-readable storage medium having embodied thereon a program executable by a processor to perform a method for monitoring health. Such program may include executable instructions for: storing user information pertaining to a user medical condition to be monitored, measuring one or more physical parameters of a user that correspond to the monitored medical condition, evaluating a medical condition of the user based on the measured physical parameters and the information pertaining to the user medical condition to be monitored that is stored in memory, and transmitting the evaluation over a wireless communication network to the devices of one or more evaluating entities. Such evaluation may include the measured physical parameters for use in further evaluating the detected medical condition.

BRIEF DESCRIPTION OF THE DRAWINGS

In order to better understand various example embodiments, reference is made to the accompanying drawings, wherein.

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

Despite the benefits associated with wearing medical alert bracelets, however, these bracelets are not usually routinely worn for many reasons. The bracelets may be extraneous and not integrated into a user's daily routine. The user may already be wearing jewelry or other devices and the addition of one or more medical alert bracelets may prove cumbersome. The medical alert bracelets may also be aesthetically unappealing. Furthermore, because of the static nature of existing medical alert bracelets, there may not be an effective means to provide recent health information such as the wearer's current medical condition. Various embodiments described herein provide improved systems and methods for conveying information about medical conditions and other related information.

Figure 1:
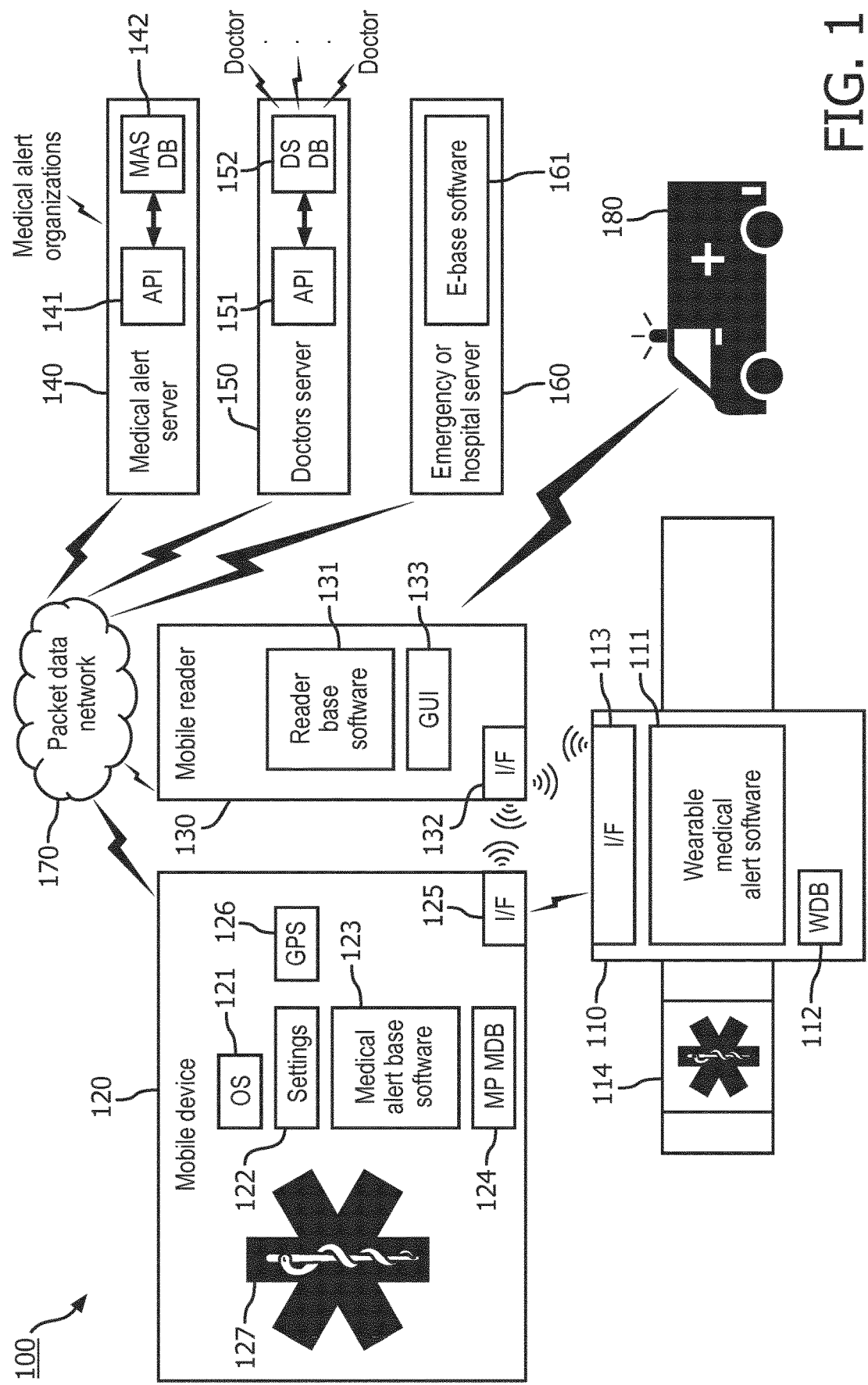
FIG. 1 illustrates an example system for raising and transmitting medical alerts.

FIG. 1 illustrates an example system 100 for raising and transmitting medical alerts. In particular, the system 100 may include a wearable device 110, a mobile device (e.g., mobile phone) 120, a mobile reader 130 and a plurality of networks 140, 150, 160. The various elements of the system 100 may be connected using a network cloud or Internet 170.

The mobile device (e.g., mobile phone, or "MP") 120 may include a variety of different elements, such as an operating system (OS) 121, settings function 122, medical alert base software 123, mobile phone medical database ("MP MDB") 124, communication interface 125 (e.g., Bluetooth, low-powered Bluetooth, Wi-Fi, 3G), and a Global Positioning System (GPS) 126. The mobile device may also include the medical alert symbol/insignia 127.

It should be noted that FIG. 1 is intended to be illustrative only. There may be other embodiments where a mobile device may include more or less of the listed elements above. Additionally, there may be embodiments that include other elements not listed above. Further, while various elements are described herein as software, instructions, functions, etc., it will be understood that such elements do not operate disembodied from hardware; instead each of the devices 110, 120, 130, 140, 150, 160 may be understood to include hardware such as one or more processors configurable to perform the described functionality though, for example, execution of instructions stored in a memory or through operation of hard-wired functions (e.g., in the case of an ASIC).

The OS 121 may be responsible for managing the various processes performed by the mobile device. In other words, the OS 121 may be instructed to monitor and proces 120s the various operations for the other elements in the mobile device 120 to provide the functionality of the mobile device 120 as described herein. In an embodiment, the OS 121 of FIG. 1 may be an existing OS known in the art (e.g., WINDOWS PHONE, GOOGLE ANDROID, or APPLE IOS operating systems).

There may be many known medical conditions that a user may be interested in having monitored. The settings function 122 of the mobile device 120 may allow the user to download one or more medical alerts specific to a medical condition of the user.

The mobile phone 120 may also include base software for a medical alert 123. The medical alert base software 123 can be responsible for facilitating the functionalities of the mobile device 120. As indicated above, different types of medical alerts may be used to monitor different conditions. The medical alert base software 123 may be adapted to monitor different conditions based on the medical alerts downloaded by the user.

The mobile device 120 may be able to communicate with other elements (e.g. mobile reader 130, wearable device 110, or various servers, e.g. medical alert server 140, doctors server 150, emergency or hospital server 160) of the overall system 100 through the use of one or more communication interfaces 125. It will be understood that while these servers 140, 150, 160 are described herein in the singular, that in various embodiments the functionality described in connection with any of these servers 140, 150, 160 may be distributed among one or more physical devices. Additionally or alternatively, one or more of the servers 140, 150, 160 may belong to a network of devices or may be implemented, at least partially, in a cloud computing environment. The mobile device 120 may communicate with the other elements through communication methods known in the art (e.g., Bluetooth, Wi-Fi, 3G, 4G).

Communication by the mobile device 120 to one or more elements may utilize various communication methods. For example, the mobile device 120 may be instructed by the medical alert base software 123 to constantly broadcast a low-powered signal (e.g. low-powered Bluetooth) that may be used as a trigger signal indicating a health (or medical) condition of the user. The use of a low-powered signal may be implemented as a way for the mobile device 120 to provide the trigger signal without using a lot of power.

The trigger signal may be used by the mobile device 120 as a way for a third party server (e.g., doctors server 150) to remotely monitor the user. The trigger signal may include information about the health condition of the user, such as sensor data obtained by a connected wearable device 110 or the data stored in the mobile device 120. The trigger signal may be updated on a regular basis based on the health condition of the user, the trigger signal can be used to inform the third party network of the health condition of the user. The third party server may evaluate the trigger signal and determine the health condition of the user. The third party server can then perform actions (e.g., nothing, calling emergency services 180, etc.) based on the trigger signal.

In various embodiments, the mobile device 120 may provide the trigger signal to a mobile reader 130 as an intermediary to one or more third party servers. In other words, an embodiment may include the mobile reader 130 that takes the trigger signal from the mobile device 120 and provides an evaluation to the third party network as to the health condition of the user.

The medical database 124 may include information about the user stored on the mobile device 120. The medical database 124 may include, for example, information (e.g., sensor data) provided by an associated wearable device 110. Information may also be downloaded from one or more networks and stored in the medical database 124. Other example types of information stored in the medical database 124 may include information about the medical condition of the user, user profile, and historic sensor data obtained and stored by the wearable device 110.

In some embodiments, the mobile device 120 may also include a global positioning system (GPS) unit 126. The GPS 126 may be used by the mobile device 120 to identify the location of the user. The location of the user may be provided in the trigger signal transmitted by the mobile device 120. The user location may also be provided when requested by a third party server. The location of the user may be used to facilitate a third party server in providing emergency services 180 to the user. For example, the emergency or hospital network 160 may use the user location to send an ambulance to the current location of the user.

A medical alert symbol 127, although not directly involved with operation of the medical alerts of the mobile device 120, may still be beneficial. In particular, as known in the art using other types of medical alert identification, the symbol 127 may be used for identifying the mobile device 120 as being a medical alert device to third parties. The third party may recognize the medical alert symbol 127 and understand that there may be information regarding the health condition of the user that can be obtained directly or indirectly from the device 120. The third party may be able to obtain information regarding the health condition of the user in situations where the user is incapacitated (e.g., fainted) or unable to talk. In some embodiments, the medical alert symbol 127 may be implemented as a sticker affixed to the mobile device 120 or a graphic displayed on the mobile device 120 that can be viewed by a third party.

The system 100 may also include a mobile reader 130. The mobile reader 130 may be used to interface with the mobile device 120 and/or a wearable device 110. For example, the mobile reader 130 may identify nearby medical alert devices and receive medical alert data (e.g., trigger signal) from the mobile device 120. A third party (e.g., first responders) who has access to the mobile reader 130 may use the mobile reader 130 to directly obtain and store information (e.g., updates on user medical condition, location) from the user.

In various embodiments, the mobile reader 130 may be a mobile device such as a mobile phone or dedicated, portable hardware for interfacing with the wearable device 110 or mobile device. Alternatively or additionally, the mobile reader may be a stationary device (e.g., a personal computer or wall-mounted emergency services device) that receives information from the wearable device 110 or mobile device 120 as these device move within communication range of the mobile reader 130.

The mobile reader 130 may include reader base software 131, communication interface 132, and a GUI 133. The reader base software 131 may be responsible for the various functionalities of the mobile reader 130. In particular, the reader base software 131 may receive various types of information (e.g., trigger signals from the mobile device 120 and/or sensor data from the wearable device 110) and determine if a user requires assistance. The reader base software 131 may forward information about the user to one or more third parties in order to obtain assistance for the user in a timely fashion. The reader base software 131 may also be capable of requesting additional information that can be used to provide assistance for the user. The additional information may include information about the user's medical condition(s) and possible treatments. For example, in an embodiment, first responders using a mobile reader 130 may obtain information about the user that can be used to evaluate the user's initial condition and provide follow-up treatment as needed.

The mobile reader 130 may also request additional information from one or more servers regarding a particular medical condition. In situations where the mobile reader 130 user is interacting with the user who may have a health condition, the mobile reader 130 can be used to access the servers to obtain more information to better educate the mobile reader 130 user when providing assistance to the user.

The communication interface 132 may be similar to the communication interface 125 of the mobile phone 120 described above. In other words, communication between the mobile reader 130 and other elements in the system 100 (e.g., mobile phone 120, wearable device 110) may be performed using methods known in the art (e.g., Wi-Fi, 3G, 4G, LTE, Bluetooth). The communication interface 132 may also be used by the mobile reader 130 to connect to the servers over the network 170.

The GUI 133 may be used by a third party to view medical alert data on the mobile reader 130. The information displayed on the GUI may include information that may be considered informative for treating the medical condition of the user. This information may be useful for the third party (e.g., emergency contact of the user, first responder) viewing the information to understand the health condition of the user. This information may be helpful in providing better treatment for the user during an initial contact between the third party and the user.

As indicated above, the wearable device 110 may also be used to facilitate monitoring a health condition of the user. The wearable device 110 may be worn by the user (e.g., via an arm band). Similar to the mobile device 120, the wearable device 110 may also forward related information (e.g., sensor data) obtained by the wearable device 110 to third parties and/or networks that can utilize the information to evaluate the health condition of the user and provide corresponding assistance and/or treatment.

The wearable device 110 may include wearable medical alert software 111, a wearable database 112 and communication interface 113. Also illustrated as being part of the wearable device 110 may be one or more medical alert identification 114 (e.g., insignia or bands) that may be incorporated on the wearable device. The wearable device 110 may include a plurality of sensors (not shown) that can be used to obtain vitals and other health parameters (e.g., body temperature, heart rate). These health parameters may be used to evaluate the health condition of the user.

The communication interface 113 of the wearable device 110 may be used to communicate information (e.g., sensor data) from the wearable device 110 to other devices (e.g., mobile device 120) in the system 100. As indicated above, the communication interface 113 may use any method known in the art to facilitate the transmission of data between the elements of the system 100 (e.g., Wi-Fi, 3G, 4G, LTE, Bluetooth, Bluetooth Low Energy, NFC). For example, the wearable device 110 may use the communication interface 113 to download information (e.g., data, applications) to be stored onto the wearable device 110. The communication interface 113 may also be used to update information already stored in the wearable device 110 (e.g., wearable database 112). The communication interface 113 may additionally or alternatively be used to repeatedly broadcast one of the various beacons described herein for receipt by one or more mobile readers 130.

In some embodiments similar to the mobile device 120, the wearable device may be configured to provide a low-powered signal (e.g., trigger signal) that can be read by third parties (e.g., networks). The signal may include information about the user and can be updated at a regular basis depending on the health condition of the user. The information may be useful for informing third parties (e.g., first responders) on how to provide initial assistance/treatment to the user. The use of low-power, as indicated above in the mobile device 120, may be implemented to conserve power required to maintain the transmission of the signal.

The medical alert software 111 of the wearable device 110 may be included to monitor and control the various functionalities of the wearable device 110. For example, the medical software 111 may be used to provide instructions to one or more sensors (not shown) on the wearable device 110 to obtain sensor data and store the obtained data in the wearable database 112. It should be noted that medical alert software 111 may instruct the sensors to obtain data targeting particular health parameters that correspond to a particular medical condition. The medical alert software 111 may also obtain sensor data on health parameters based on the interest of the user or the doctor to view such parameters.

In an embodiment, the medical alert software 111 may request medical assistance based on the sensor data obtained. For example, the medical software 111 may assign a threshold value to one or more sensors or to calculated parameters based on the sensors (e.g., heart rate, blood pressure, or averages thereof over a time period). In situations where sensor data obtained from the plurality of sensors, parameter values, or other relevant data exceeds the threshold value(s) or are otherwise determined to indicate a medical emergency, the wearable device 110 may utilize the medical alert software 111 to provide the related information and a request for assistance for the user directly to, for example, a hospital or medical professional (e.g., doctor). It will be apparent that threshold comparison is only an example of a way to identify a trigger for requesting medical assistance based on received sensor data. Alternative trigger types will be apparent such as, for example, presence or absence of sensor data (user depressing a panic button, lack of pulse data, etc.) or identification of an emergency event (e.g., identification of a seizure through observation of accelerometer data).

Similar to the medical alert sticker 127 of the mobile device 120, the medical alert identification 114 on the wearable device 110 may be used to identify the wearable device 110 as being a medical alert device. In other words, the medical alert identification 114 may be used to inform others that there may be information about the health condition of the user on the wearable device 110 that can be used to assist or treat the user.

According to various embodiments, the wearable device 110 or mobile device 120 may repeatedly (e.g., constantly or periodically) broadcast medical alert information to be received by one or more mobile readers. As such, the wearable device 110 or mobile device 120 may act as a beacon to be read by the mobile reader 130 when in range, thereby providing important information such as patient conditions; name and other demographics; emergency contact information; current, recent, or historical sensor readings; or identification of recent health-related events. In various embodiments, the wearable device 110 or mobile device 120 may always (e.g., whenever powered on) broadcast the medical alert information while, in other embodiments, the wearable device 110 or mobile device 120 may only begin the repeated broadcasting of medical alert information when it has determined that a medical emergency exists (e.g., in response to the occurrence of one or more triggers, examples of which will be described in greater detail below with respect to FIG. 7). In some embodiments, the wearable device 110 or mobile device 120 may always broadcast information while determination that a medical emergency exists may prompt the wearable device 110 or mobile device 120 to change what information is being broadcast. As used herein, "repeated transmission" will be understood to refer to the transmission of data in a repeated manner without an external trigger to initiate each individual transmission. As such, "repeated transmission" does not merely entail every possible scenario involving transmission of information multiple times regardless of context, but rather refers to the automatic repetition of the transmission.

According to the operation described above, the wearable device 110 or mobile device 120 may replace and improve upon existing medical alert bracelets. For example, when a first responder arrives to provide assistance to the user, a mobile reader 130 carried by the first responder (e.g., in hand, in the first responder's pocket such as in the case where the mobile reader 130 is a mobile device of another party, or within a vehicle of the first responder) may receive the broadcast medical alert information and provide it to the first responder. The mobile reader 130 may alert the first responder to the receipt and availability of the medical alert information through, for example, an audible or vibrational signal.

Because the sending device includes or is otherwise in communication with a wearable sensor, the medical alert information may also include dynamic health parameters that may be useful to the first responder. As used herein, the term "health parameter" will be understood to include both sensed parameters received various sensors as well as calculated parameters (including identified events) determined based, at least in part, on the sensed parameter. For example, where the wearable device 110 or mobile device 120 is configured to indicate that the user has a heart disease medical alert, the wearable device 110 or mobile device 120 may broadcast measured pulse and blood pressure parameters so that his information is immediately available to the first responder. As another example, where the wearable device 110 or mobile device 120 is configure to indicate that the user has an epilepsy medical alert, the wearable device 110 or mobile device 120 may broadcast measured accelerometer parameters or an indication that the patient has experienced a seizure. Additionally, where the wearable device 110 or mobile device 120 broadcasts an indication of a seizure, this indication may be accompanied by additional calculated parameters about the seizure such as, for example, seizure duration or intensity, as calculated from recent accelerometer sensor data.

It will be understood that use of the mobile reader 130 by a first responder is only one example of a potential use, and that the mobile reader 130 may be useful in other contexts. For example, one or more mobile readers 130 may be provided in a hospital emergency waiting room or triage room to provide the medical alert information to medical staff in a manner similar to that described with respect to first responders. Similarly, mobile readers 130 may be provided in other rooms of the hospital as well as in other facilities such as, for example, physicians' offices, schools, airports, or virtually anywhere that medical alert information may be useful in case of a medical emergency.

In some embodiments, various mechanisms may be employed to protect the privacy of the medical alert information being transmitted by the mobile device 120 or wearable device 110. For example, the medical alert information may be transmitted in an encrypted form and may be decrypted by the mobile reader 130 using a key received from the mobile device 120 or wearable device 110 during a handshaking process, using a private key of the mobile reader 130, using a key received from a third party server, or using a key defined by or generated according to a standard associated with the transfer of medical alert information between the illustrated devices 110, 120, 130.

In some embodiments, rather than broadcasting the medical alert information itself, the wearable device 110 or mobile device 120 may instead broadcast an indicator that such information is available upon request. The form of such an availability message may be predetermined and agreed upon by the devices 110, 120, 130 such as, for example, by a standard governing the interaction of these device 110, 120, 130. Upon receiving such an indication, the mobile device 130 may automatically or upon request by the mobile reader 130 user, request that the wearable device 110 or mobile device 120 provide the medical alert information. In some embodiments, the availability indicator or medical alert information may not be broadcast and instead may be multicast o unicast to one or more mobile readers 130 based on, for example, a previous pairing or handshake between the mobile reader 130 and the wearable device 110 or mobile device 120. In various embodiments, the wearable device 110 or mobile device 120 may transmit over an unlicensed band (e.g., 13.56 MHz, 2.4 GHz, 5 GHz bands) or may be transmitted over a licensed band such as, for example, other portions of industrial, scientific, and medical bands (ISM) defined by various governing bodies (e.g., the U.S. Federal Communications Commission (FCC) or International Telecommunication Union (ITU)).The system 100, illustrated in FIG. 1, may include a plurality of different servers. Example servers may include a medical alert servers 140, a doctors servers 150 and an emergency or hospital servers 160. It should be noted that other servers may also be included in the system of 100 not described herein but may be also used to facilitate the features of the present invention. Additionally, while various embodiments are described as including a single server to perform a group of functions, it will be understood that one or more of the servers 140, 150, 160 may belong to networks of multiple servers or other network equipment and that the various functionalities described herein may be divided among multiple devices. Additionally, one or more devices corresponding to a server may be hosted in a cloud computing environments as, for example, a virtual machine.

Each of the plurality of networks may include an application programming interface (API) 141 and an associated database 142, e.g. medical alert server database (MAS DB). The API may be implemented to facilitate access to information stored in the database 142. The API 141 may also facilitate the storage and update of information stored in the database 142.

It should be noted that an authentication method (e.g., password) may be implemented in a particular server to control the parties capable of editing the information stored in the network. Alternatively, other forms of identification can be used to identify whether an individual has the experience/specialty useful for updating information in a database. In another embodiment, a third party (e.g., hospital) may directly monitor and manage the database of a particular server. The third party may restrict who can edit the database.

In an example embodiment, the medical alert server 140 may be directed towards a particular medical condition. The medical alert server database 142 may include information related to that medical condition (e.g., symptoms, information about the medical condition, treatment/medicine, emergency contacts). The API 141 may be used by medical professionals (e.g., doctors) to not only access the data stored in the database 142 but also to update and add to the data stored in the database 142.

The doctors server 150 may include contact information (e.g., phone numbers, websites) as well as profile information (associated hospitals and networks) for a plurality of doctors. The doctors stored in the doctors server's database 152 may include all available doctors in the server (nor network associated therewith). In an embodiment, the doctors listed in the doctors server 150 may include their specialties so that an appropriate doctor may be contacted in view of a particular medical condition. For example, if the user is suffering from a heart condition, a doctor who specializes in heart conditions may be contacted for assistance. It should be noted that the information regarding a particular doctor in the doctors server 150 may be accessed and modified from the database 152 through the use of the API 151.

Also illustrated in FIG. 1 is the emergency or hospital server 160. The emergency or hospital server 160 may correspond to a particular hospital. Through the use of the server 160, a hospital may receive information from a plurality of different users. The users may provide the emergency or hospital server 160 with information through the use of the various devices described above (e.g., wearable device 110, mobile device 120 or the mobile reader 130).

The e-base software 161, included in the emergency or hospital server 160, may evaluate information from various users and determine which users may need immediate assistance. The hospital may then access the related information stored in the emergency or hospital server 160. Based on the accessed information, the hospital may begin appropriate steps in providing assistance and treatment for a user. In an embodiment, the emergency or hospital server 160 may contact emergency services 180 to tend to the user and provide initial treatment and assistance.

Figure 2:
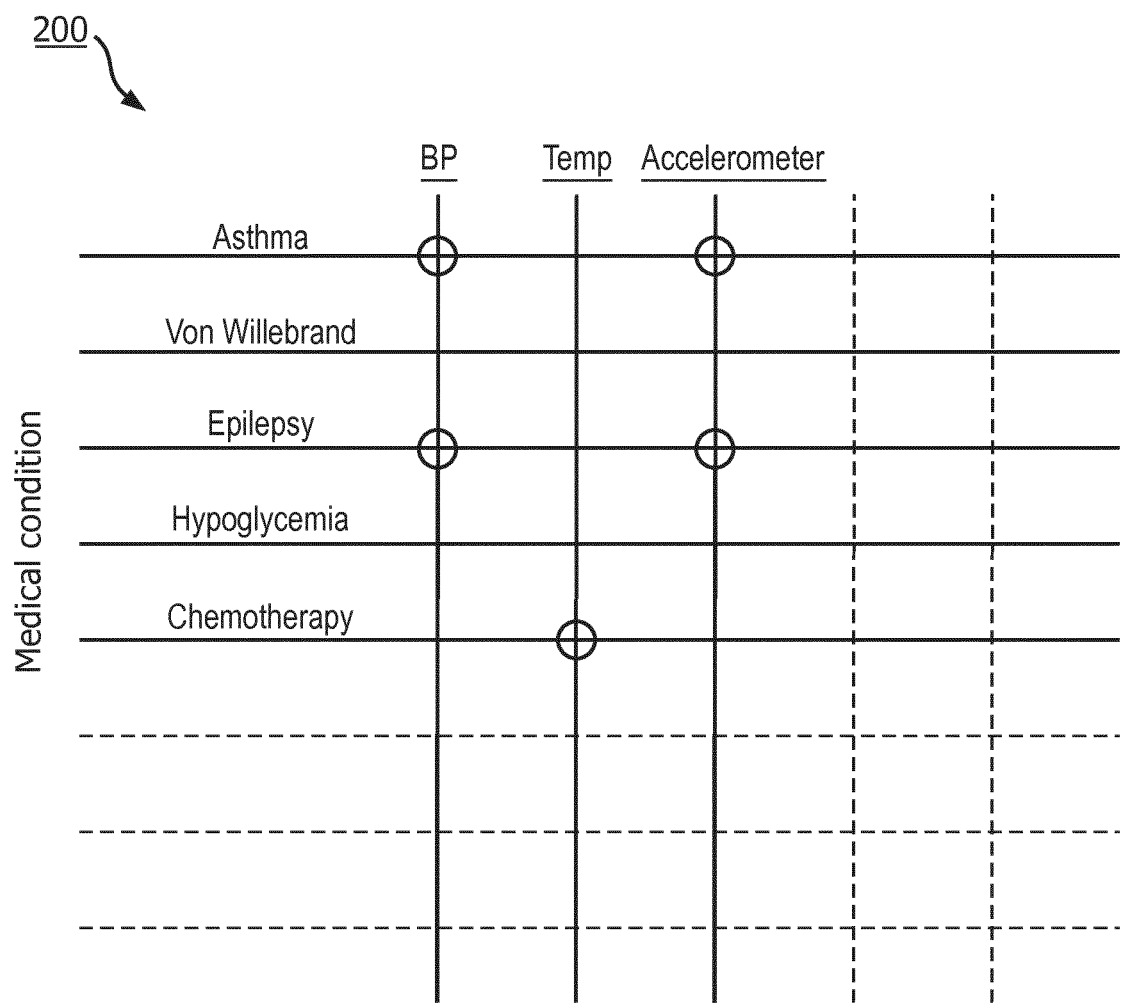
FIG. 2 illustrates example medical conditions and the corresponding sensors used to detect the medical conditions.

FIG. 2 illustrates an example correspondence between medical conditions and sensors used to monitor the medical conditions. There may be many different medical conditions known in the present day. The medical alert server may include information for each of those known medical conditions. FIG. 2 illustrates some example medical conditions including asthma, epilepsy and hypoglycemia. FIG. 2 also illustrates examples of corresponding sensors (e.g., blood pressure sensor, temperature sensor, accelerometer) that may be used to monitor and measure the example medical conditions. It should be noted that there are many different types of medical conditions known in the world and that the present invention may monitor those different medical conditions not described here as well. Additional sensors not shown in FIG. 2, furthermore, may also be included in embodiments of the present invention to monitor and measure sensor data related to the medical conditions.

The grid 200 illustrated in FIG. 2 shows example correlation between some medical conditions and a corresponding set of sensors that can be used to monitor or detect the medical condition. For example, as seen in FIG. 2, by measuring motion (using the accelerometer) and blood pressure (using a blood pressure sensor), the present invention is capable of monitoring and detecting asthma in the user. In particular, the sensors are capable of obtaining sensor data from the user. The sensor data can then be used to determine if an asthma attack is possible. The use of the sensor data can inform the user and/or medical professionals to proceed with preventative measures that can be used to reduce or eliminate the medical condition.

Figure 3:
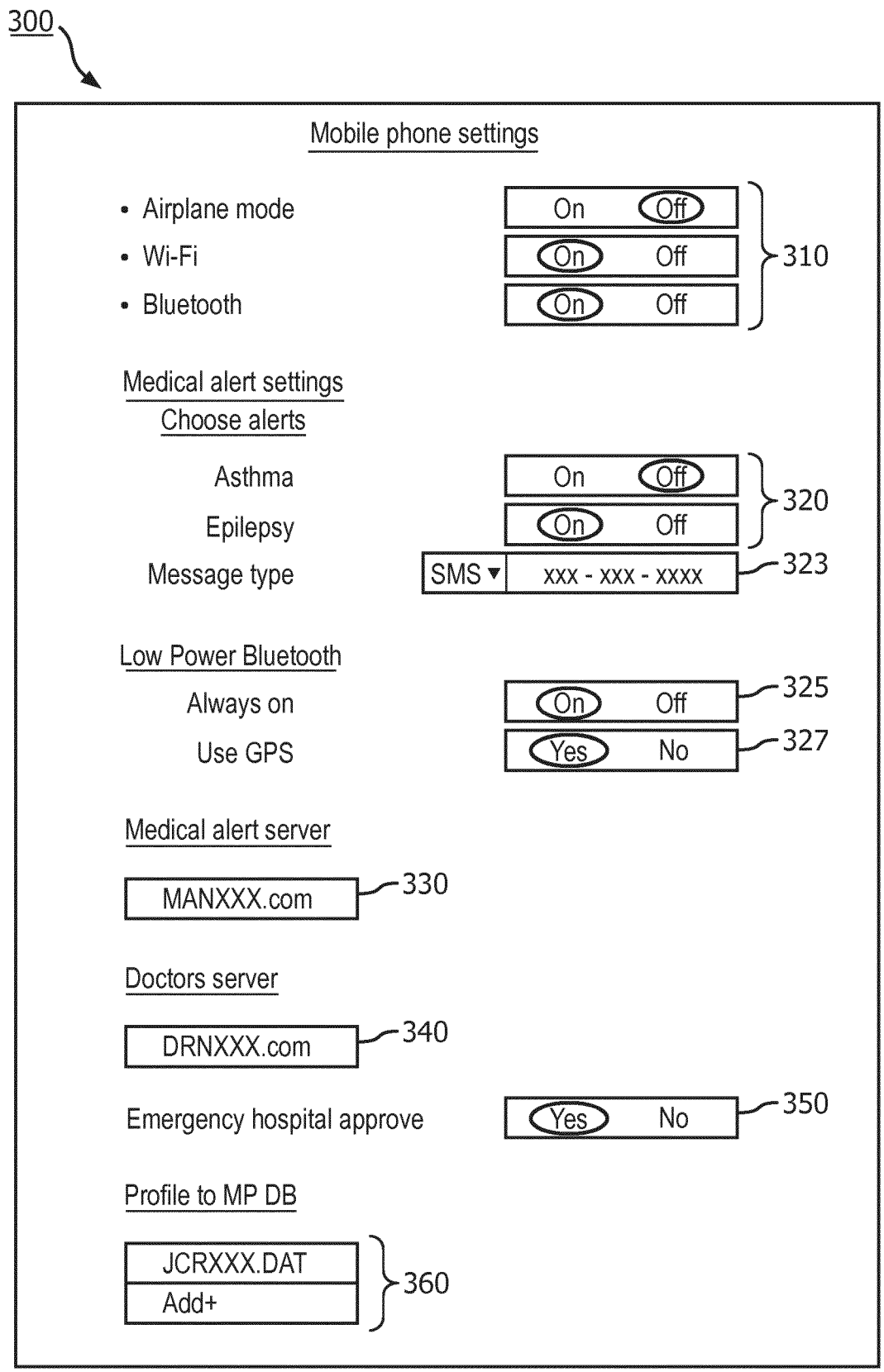
FIG. 3 illustrates an example mobile device settings GUI.

FIG. 3 illustrates an example mobile device settings GUI 300. The mobile device of FIG. 3 may be a variety of different types of mobile devices including mobile phones, tablets or a laptop. In various embodiments, the GUI 300 may be provided by a processor executing the settings software 122 of FIG. 1.

As illustrated in the figure, the GUI 300 may include a variety of settings that the user may interact with to customize operation of the mobile device. Some example settings (e.g., phone settings 310) may be settings that can be found on various mobile devices (e.g., airplane mode, Wi-Fi and Bluetooth). These settings may operate in a similar manner as known in the art for turning on and off airplane mode, as well as Wi-Fi and Bluetooth connectivities.

The GUI 300 may also include settings directed to particular medical alert settings 320. For example, the medical alert settings 320 may allow the user to select one or more particular medical conditions to monitor. In FIG. 3, an example user has selected that epilepsy is a medical condition the user wishes the mobile device to monitor. The mobile device may then monitor the health condition of the user and inform appropriate parties (e.g., networks, third parties) if epilepsy is possibly detected.

FIG. 3 illustrates that asthma and epilepsy are two possible medical conditions that could be monitored. It should be noted that many more and different types of medical conditions may also be incorporated and selected in the settings 320. In other embodiments, the user also may be able to instruct the mobile device to monitor a particular medical condition by providing an input into the GUI using one or more keywords corresponding to medical conditions. The keywords may be recognized by the user device and may initiate monitoring of the inputted medical condition. There may be additional embodiments where more than one medical condition is monitored at a time.

After the medical condition is selected, the user may also determine what type of message may be provided and to where the message should be sent via a message field 323. For example, the message may be used to inform one or more receivers via one or more communications channels that the user is currently suffering from a particular medical condition and may need assistance. Alternatively, the message could be provided to third parties (e.g. the doctors server or to an emergency contact) to inform the third party of the present medical condition being experienced by the user.

Many different types of messages can be included based on the medical condition that triggered the sending of the message. For example, the user may input personal messages prepared beforehand in anticipation of a possible medical condition. The personal message may include information about nearby medicine that can be used. The personal message may also include general treatment advice that may be helpful to non-medical professionals when dealing with the medical condition.

The GUI 300 may also include options for the user to configure how communication is performed using the Bluetooth communication settings 325 of the mobile device. In the embodiment of FIG. 3, the Bluetooth communication setting 325 can request an indication by the user whether the mobile device should always be transmitting information about the health condition of the user (e.g., trigger signal). The user may be able to turn off the constant transfer of information in situations where such information transfer is not necessary.

The user may also be able to indicate whether the user location could be obtained through the use of the associated GPS (e.g. "Use GPS" of settings 327). As indicated above, the location of the user may be helpful in providing quick assistance by third parties (e.g., first responders). The location of the user can inform third parties (e.g., first responders) where the user is. The location of the user may also be helpful in selecting which networks the mobile device sends the trigger signal to. For example, the user may be transmitting information to the closest hospital or medical professional (e.g., doctor).

The user may also be able to input the identification of one or more medical alert servers 140 via settings 330 and/or one or more doctors servers 150 via settings 340 that the user is interested in sending information to. By selecting particular medical alerts servers via settings 330 and/or doctors servers via settings 340, the user may be able to ensure that the information is being sent to a medical alert server 140 and/or doctors server 150 that specializes in monitoring and/or treating the medical condition of the user. The user may also provide the identification of medical alert servers 140 and/or doctors servers 150 associated with services that can be received locally from where the user is. The user may be able to input the identification of the medical alert servers 140 and/or doctors servers 150 into the GUI 300 (e.g., via touch screen). In another embodiment, a menu may list all available nearby medical alert servers and/or doctors servers from which the user can select from. In yet another embodiment, the profile may automatically populate itself with medical alert servers 140 and/or doctors servers v150 that are nearby and/or possess relevant skills.

The GUI 300 may also include features where the user can authorize emergency hospital care via emergency hospital approve setting 350. This setting 350 may be directed towards providing approval for servers (e.g., hospitals) to download information about the user including medical history and profile of the user and information about the medical conditions. The medical information about the user may be stored, for example, on the user mobile device and/or synchronized with the user wearable device. The use of this information may facilitate the treatment of the medical condition of the user by first responders and other medical professionals.

The user may also be able to define how data is stored in the mobile device via data settings 360, e.g. Profile to MP DB. In particular, the feature in the GUI 300 may describe what data is stored in the mobile device and how it is stored. For example, sensor data obtained from the wearable device may be instructed to be stored in the mobile device database associated with a particular user profile. The user profile name may be provided in the GUI 300. The user may also be capable of creating multiple accounts for different users.

It should be noted that other features may be implemented in the GUI 300. FIG. 3 is intended as being an example GUI that shows some features that can be implemented in an embodiment of the present invention. Other options for customizing, for example, operation of the mobile device, interactions with the other elements in the system of the present invention, how the data is obtained by the wearable device, stored in memory and transmitted to other parties, may also be implemented in other embodiments.

Figure 4:
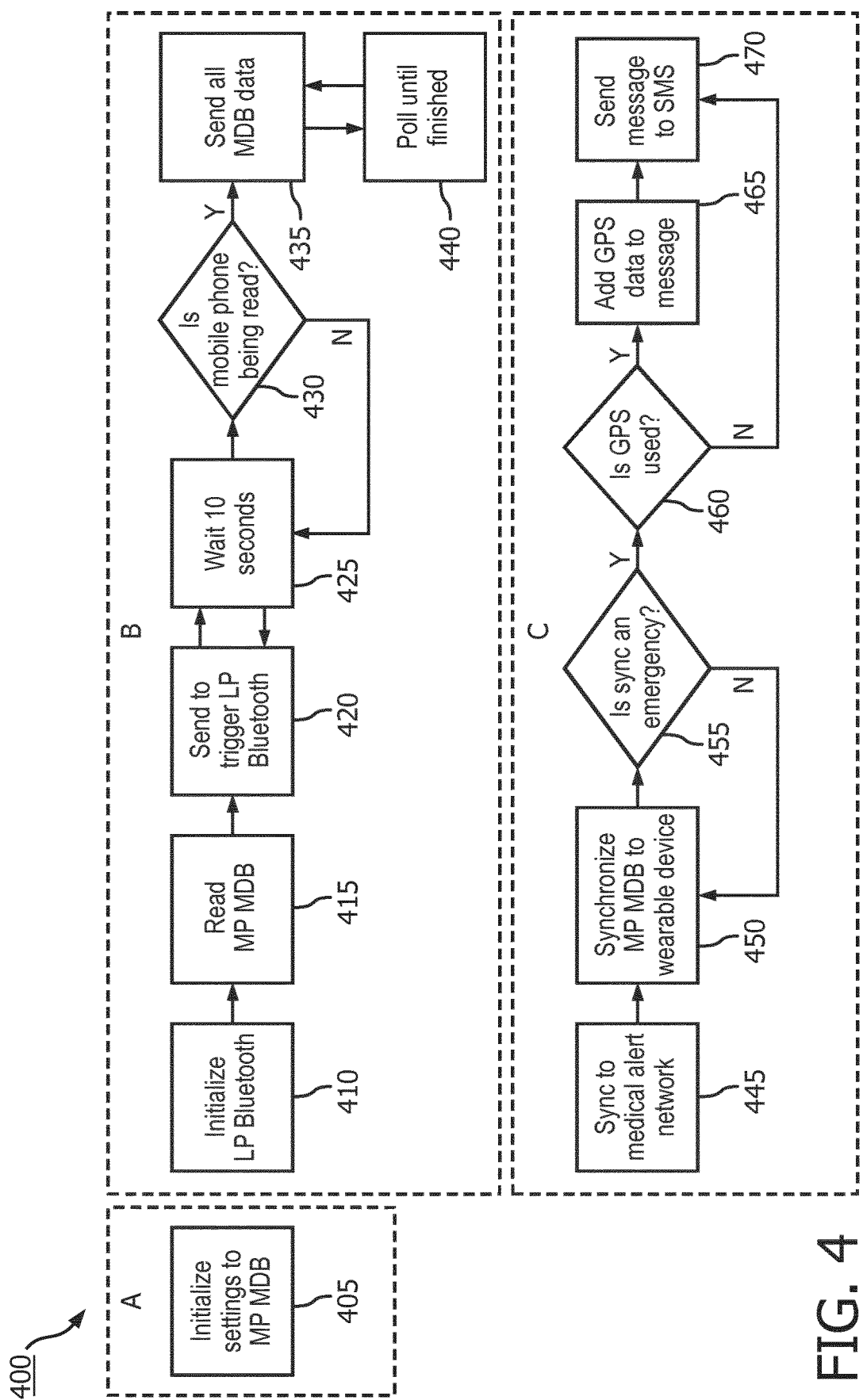
FIG. 4 illustrates example medical alert base software on the user mobile device.

FIG. 4 illustrates example medical alert base software on the user mobile device. In particular, the medical alert base software 400 includes three parts (identified in FIG. 4 as A, B and C).

In the first part of the medical alert base software 400 (identified as A in FIG. 4), there may be one or more steps directed at initializing the medical alert base software. In particular, in step 405, the user may initialize one or more settings for the mobile device, e.g. "Initialize Settings to MP MDS." These settings may then be stored in the main database of the mobile device. This step may be performed with the GUI 300 described above in FIG. 3.

The second part of the medical alert base software 400 (identified as B in FIG. 4) may correspond to an operation of the medical alert software 123 of FIG. 1. The second part corresponds to providing notification to one or more third parties and/or networks that can be used to monitor the health condition of the user.

In step 410, the user may initialize the communication interface of the mobile device, e.g. "Initialize LP Bluetooth." The user may indicate that communication can commence by "turning on" the communication interface. The user may also be capable of selecting how communication is performed. For example, the user may indicate that the use of a low-powered signal (e.g., low-power Bluetooth) may be desired in order to provide a constant trigger signal without expending a lot of energy while doing so.

In step 415, the mobile device may access the main database of the mobile device, e.g. "Read MP MDB." The main database may include information on the health condition of the user obtained from one or more sources. For example, the wearable device of the user may transmit information to the mobile device and the information may be subsequently stored in the main database for future reference.

Based on the information stored in the main database, the mobile device may provide a trigger signal to one or more intended recipients. In step 420, the mobile phone may be instructed to provide a trigger signal to, for example, a doctor or health network, e.g. "Send to Trigger LP Bluetooth." The trigger signal may include information in the main database of the mobile device that summarizes the current health condition of the user. In an embodiment, the trigger signal may be updated and re-transmitted on a continual or repeated basis (e.g., every 10 seconds) so that the servers and/or medical professionals receiving the trigger signal may be sure that they are obtaining the most up-to-date information possible to most accurately evaluate and treat the medical condition of the user.

As noted above, the trigger signal may be provided through the use of communication methods known in the art. For example, the user may select use of a low power signal in order to facilitate transmitting the trigger signal over a long period of time using as little power as possible.

As indicated above, the trigger signal may be updated and retransmitted at regular intervals. In step 425, the medical alert base software performs the update and retransmission every ten seconds, e.g. "Wait 10 Seconds." The updates and retransmission can ensure that the most up-to-date information regarding the health condition of the user is provided. In some embodiments, the method 400 may provide an updated trigger signal every ten seconds. The retransmission may be provided repeatedly (e.g., looping between steps 420,425) until, for example, the trigger signal is read by a third party using a mobile reader. In another embodiment, the trigger signal may be provided for a set duration. Once the duration has elapsed, the mobile device may be instructed to stop transmission of the trigger signal.

In step 430, the medical alert base software performs a check to evaluate if the trigger signal has been read, e.g. "Is Mobile Phone being Read?" This check may be performed continuously while the medical alert base software is active. This check may also be performed for a short time following a retransmission of the trigger signal. Regardless of how the check is performed, the medical alert base software may poll for a notification from a device or network that received the trigger signal.

The notification, if received by the mobile device, can inform the identification of the third party or server that is interested in obtaining the information about the user. In step 435, the medical alert database receives a notification from a possible network or third party and proceeds to transmit related information (e.g., "Send All MDB Data," including medical history, current sensor data) stored in the main database of the mobile device to the third party or network. The third party or network may utilize the information to evaluate the health condition of the user and perform appropriate support and treatment. The medical alert base software may terminate once all the related health condition user information has been transmitted, for example in step 440, the medical alert base software may poll for a confirmation from the recipient third party or network that the transmission has been completely received.

The third part of the medical alert base software 400 (identified as C) shows steps for downloading information to the wearable device. In step 445, the mobile device first connects with the medical alert network, e.g. "Sync to Medical Alert Network." The mobile device may then perform synchronization with the medical alert network to obtain any information that may be out of date or missing from the mobile device. In particular, the mobile device may access and download particular information from the medical alert network.

In step 450, the mobile device can synchronize with the associated wearable device, e.g. "Synchronize MP MDB to Wearable Device." For example, information stored in the main database of the mobile device may be transmitted to the wearable database in the wearable device. The information transmitted to the wearable device may include information about particular medical conditions that the user may be experiencing. The information can be used to instruct one or more sensors associated with the wearable device to monitor particular parameters so that the medical condition can be evaluated and detected.

In step 455, a check may be performed by the medical alert base software to determine if synchronization between the mobile device and the wearable device was conditioned of an existing emergency condition of the user, e.g. "Is Sync an Emergency?" The emergency condition may correspond to a currently existing medical condition of the user that has been detected or that a medical condition is expected to occur in the near future.

If a determination is reached that an emergency condition is present, the medical alert base software may then determine if the wearable device has GPS available in step 460, "Is GPS Used?" As indicated above, GPS may be beneficial in determining where the user is located. The location of the user can be used to direct assistance and treatment to the user, especially in situations where the user is unable to seek out help by themselves.

In step 465, the location of the user can be incorporated into a message indicating that an emergency is present, e.g. "Add GPS Data to Message." The message may include information about the user and the medical condition detected. The message may also include a request for assistance or treatment from the user directed at a particular doctor or hospital.

The message can be provided to one or more parties using, for example, a short message service (SMS) for notification of the medical condition as seen in step 470, e.g. "Send Message to SMS." Alternatively, a phone call can be provided to, for example, emergency contacts, hospitals, doctors, etc., along with the message about the emergency. If no emergency exists, then the base software can synchronize the information between the mobile device and the wearable until an emergency occurs. In various embodiments, the message may be sent in step 470 according to settings input by the user such as, for example, via the message input 323 of example GUI 300.

Figure 5:
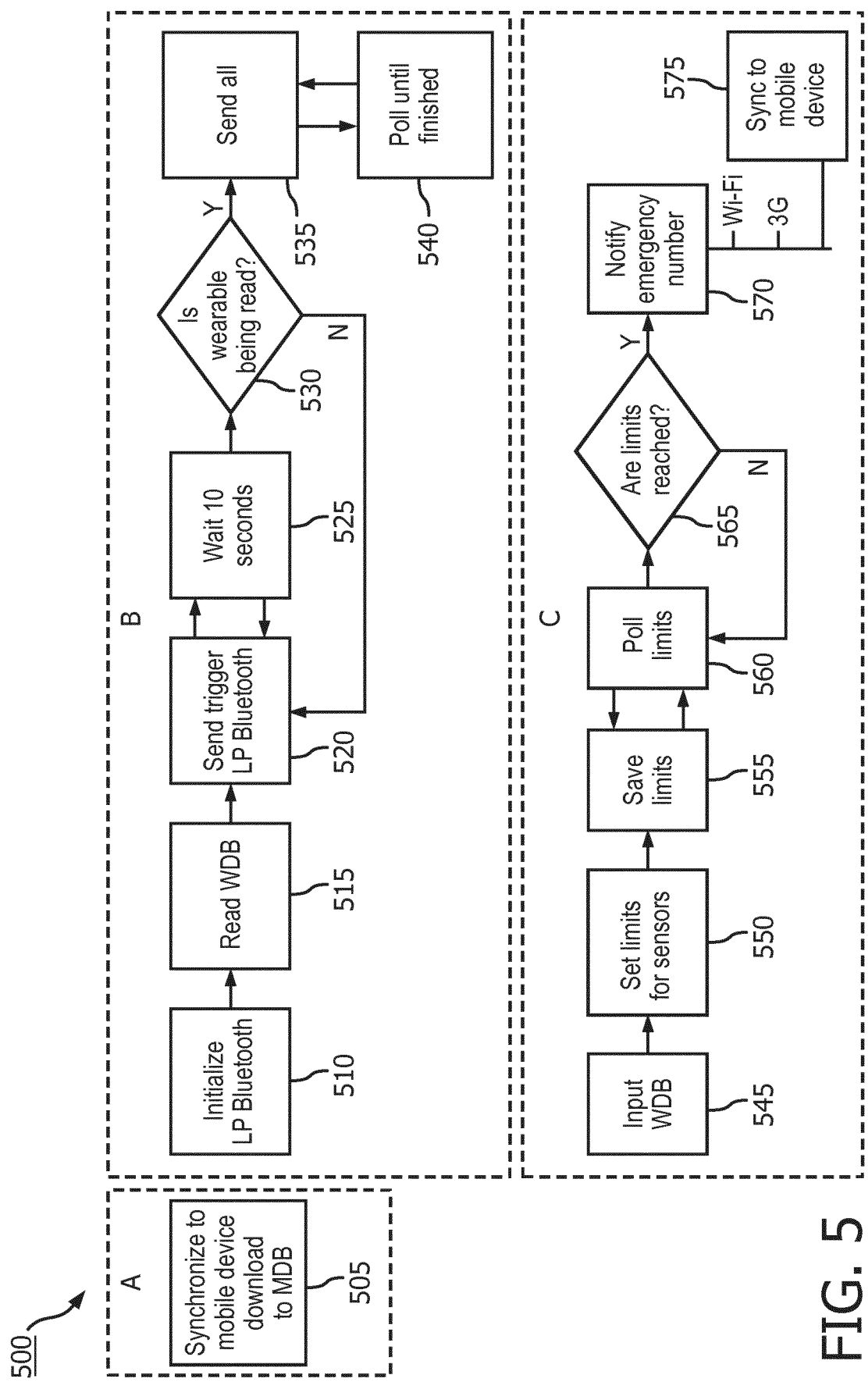
FIG. 5 illustrates example medical alert software found on the user wearable device.

FIG. 5 illustrates example medical alert software 500 found on the user wearable device. As seen in the medical alert base software 400 on the user mobile device in FIG. 4, the medical alert software 500 found on the user wearable device can also be identified as three parts (identified as A, B and C). In various embodiments, the example medical alert software 500 may correspond to the wearable medical alert software 111 of FIG. 1.

With regards to the first part, identified as A, step 505 of the medical alert software is directed towards a synchronization of the medical database of the mobile device with the wearable database found in the wearable device. This step may correspond to the above step similarly described in step 450 of FIG. 4.

The second part, identified as B, is directed towards what the medical alert base software of the wearable device may be doing on an ongoing basis. Steps 510, 515, 520, 525, 530, 535, 540, directed at initializing communication in the wearable device and providing a consistent updated trigger signal, may be similar to steps 410-440 described above in FIG. 4.

Although the steps are performed here in the wearable device as opposed to the mobile device, the function and purpose of the steps may be similar. In particular, the wearable device is providing information about the health condition of the user constantly through the use of the trigger signal. Upon receipt of a request for additional information from a network or third party performing a read on the trigger signal, the wearable device (through the medical alert base software) may transmit user profile information and information about the health condition of the user to the network or third party that is interested in obtaining the additional information.

In the third part of the software, identified as C, the medical alert base software 500 may be directed at managing the wearable device for monitoring the health condition of the user. In step 545, the medical alert base software 500 may use information stored in the wearable database. The information stored in the wearable database may include user profile information, background medical history of the user and possible medical conditions that can be monitored.

In step 550, the medical alert base software 500 may set threshold limits for the one or more sensors associated with the wearable device. These threshold limits may be provided by the user through the use of a GUI. In another embodiment, these threshold limits may be set by the medical alert base software 500 based on the information stored in the wearable database. As noted above, there may be existing medical information related to particular medical conditions. The medical alert base software 500 may be capable of extracting relevant information and implementing the information accordingly with respect to the sensors. The wearable database may also include limits provided by one or more networks or from medical professionals (e.g., doctors).

Once the threshold limits for the sensors have been set, the threshold limits for one or more sensors may be saved in step 555. The threshold limits may be saved in the wearable database for future reference.

In step 560, sensor data is obtained from one or more sensors on the wearable device. The medical alert base software may then evaluate the sensor data (in step 565) and compare the sensor data with the threshold limits stored in the wearable database. The medical alert base software may continually monitor the sensor data to ensure that the sensor data stays within an accepted range. In a situation where sensor data exceeds a threshold limit, this may be indicative of a medical condition.

For example, a threshold limit for body temperature may be placed at 100° F. In a situation where the wearable device obtains a sensor data for the user body temperature over 100° F., this may be indicative of the user having a fever. It should be noted that there may be various limits and parameters that can be monitored and evaluated to detect one or more medical conditions.

In a situation where a threshold limit has been reached, in step 570, the medical alert base software may be instructed to provide notification to one or more parties (e.g., emergency contacts, hospitals, doctors). As indicated above, the threshold limit may be indicative of a medical condition. Therefore, notification may be necessary to request assistance and/or treatment in a timely manner. The wearable device may be able to provide the notification of a possible medical condition through its own communication interface using methods known in the art (e.g., Wi-Fi, 3G, 4G, LTE, Bluetooth). The notification may include the user profile information, sensor data obtained, related threshold limits exceeded, user location obtained through the GPS and a request for specific assistance or treatment.

In step 575, the wearable device may also synchronize with a corresponding user mobile device. The synchronization may be implemented to assist in the relay of the emergency notification in step 570. For example, the wearable device may not capable of connecting to the Internet at a current time. Through the use of the user mobile device, the request from the wearable device may be transmitted from the wearable device to the mobile device and afterwards to a desired network over the Internet.

Figure 6:
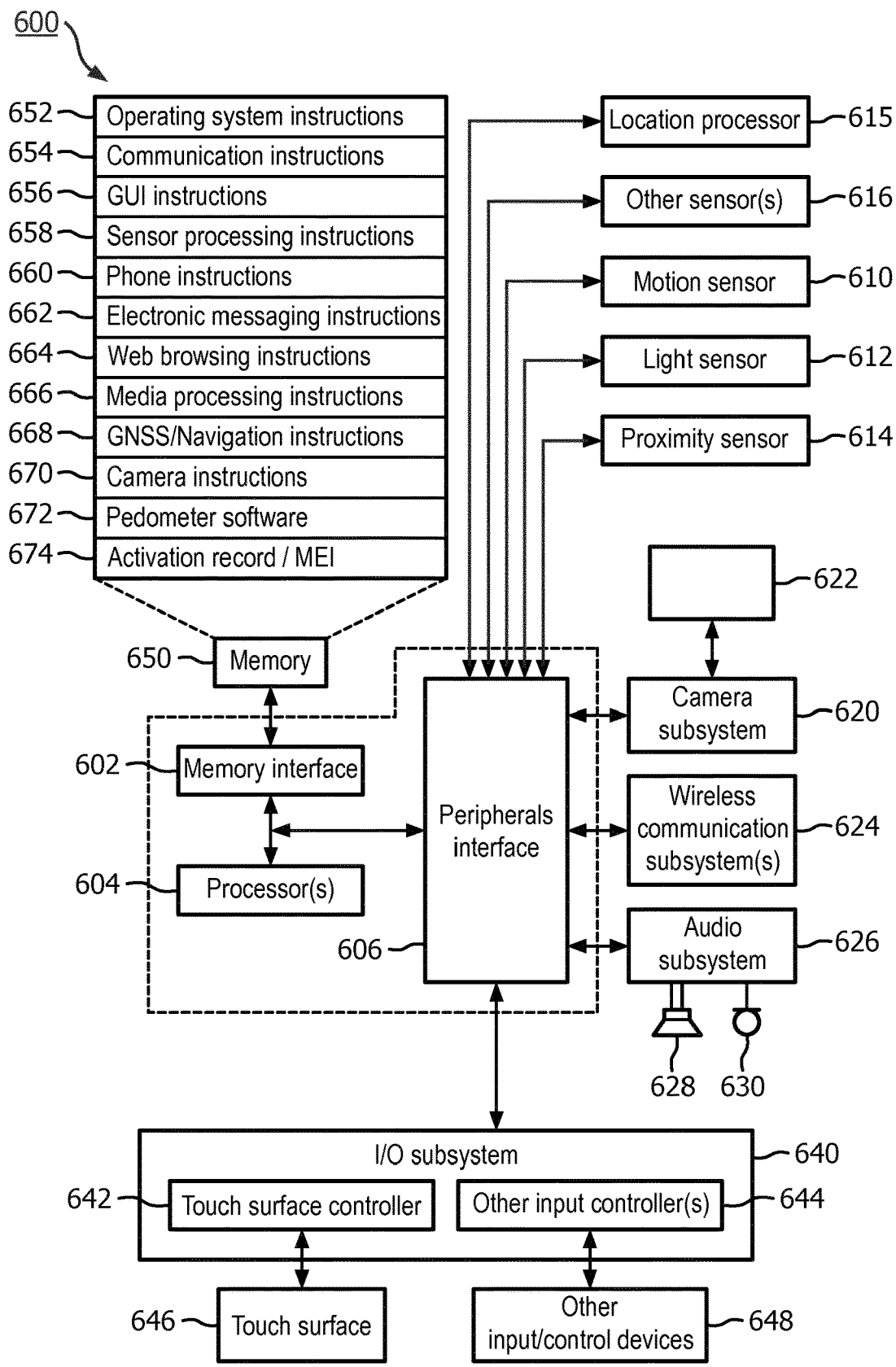
FIG. 6 illustrates an example computing device architecture that may be utilized to implement the various features and processes.

FIG. 6 illustrates an example computing device architecture 600 that may be utilized to implement the various features and processes described herein. In various embodiments, the architecture may correspond to the wearable device 110, mobile device 120, or mobile reader 130 of FIG. 1. For example, the computing device architecture 600 could be implemented in a pedometer. Architecture 600 as illustrated in FIG. 6 includes memory interface 602, processors 604, and peripheral interface 606. Memory interface 602, processors 604 and peripherals interface 606 can be separate components or can be integrated as a part of one or more integrated circuits. The various components can be coupled by one or more communication buses or signal lines.

Processors 604 as illustrated in FIG. 6 is meant to be inclusive of data processors, image processors, central processing units, or any variety of multi-core processing devices. The processors 604 may be virtually any device capable of performing the functions described herein. For example, the processors 604 may include one or more microprocessors, one or more field-programmable gate arrays (FPGA), or one or more application-specific integrated circuits (ASIC). In some embodiments, the processor may not utilize stored instructions to perform some or all of the functions described herein; for example, an ASIC may be hardwired to perform one or more of the functions described herein.

Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be exemplified in the context of an accelerometer or gyroscope, could be utilized to detect movement and orientation of the mobile device. Display objects or media could then be presented according to a detected orientation (e.g., portrait or landscape).

Other sensors could be coupled to peripherals interface 606, such as a temperature sensor, a heart rate sensor, a blood pressure sensor, a blood-glucose sensor, or other sensing device to facilitate corresponding functionalities. Location processor 615 (e.g., a global positioning transceiver) can be coupled to peripherals interface 606 to allow for generation of geo-location data thereby facilitating geo-positioning. Other sensors 616 such as an electronic magnetometer such as an integrated circuit could be connected to peripherals interface 606 to provide data related to the direction of true magnetic North whereby the mobile device could enjoy compass or directional functionality. Camera subsystem 620 and an optical sensor 622 such as a charged coupled device (CCD) or a complementary metal-oxide semiconductor (CMOS) optical sensor can facilitate camera functions such as recording photographs and video clips.

Communication functionality can be facilitated through one or more communication subsystems 624, which may include one or more wired or wireless communication subsystems. Wireless communication subsystems 624 can include 802.x or Bluetooth transceivers as well as optical transceivers such as infrared. Wired communication subsystems can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.x communication networks, code division multiple access (CDMA) networks, or Bluetooth networks. Communication subsystem 624 may include hosting protocols such that the device may be configured as a base station for other wireless devices. Communication subsystems can also allow the device to synchronize with a host device using one or more protocols such as TCP/IP, HTTP, or UDP.

Audio subsystem 626 can be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 can be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 can display virtual or soft buttons and a virtual keyboard, which can be used as an input/output device by the user.

Other input controllers 644 can be coupled to other input/control devices 648 such as one or more buttons, rocker switches, thumb-wheels, infrared ports, USB ports, and/or a pointer device such as a stylus. The one or more buttons (not shown) can include an up/down button for volume control of speaker 628 and/or microphone 630. In some implementations, device 600 can include the functionality of an audio and/or video playback or recording device and may include a pin connector for tethering to other devices.

Memory interface 602 can be coupled to memory 650. Memory 650 can include high-speed random access memory or non-volatile memory such as magnetic disk storage devices, optical storage devices, or flash memory. Such memories will be understood to constitute "non-transitory machine-readable media." As used herein, the term "non-transitory" will be understood to exclude transitory signals but to include all forms of information storage, including both volatile and non-volatile memories. Memory 650 can store operating system 652, such as Darwin, RTXC, LINUX, UNIX, OS X, ANDROID, WINDOWS, or an embedded operating system such as VxWorks. Operating system 652 may include instructions for handling basic system services and for performing hardware dependent tasks. In some implementations, operating system 652 can include a kernel.

Memory 650 may also store communication instructions 654 to facilitate communicating with other mobile computing devices or servers. Communication instructions 654 can also be used to select an operational mode or communication medium for use by the device based on a geographic location, which could be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; pedometer software 672 to process data received from a pedometer sensor; activation record or international mobile station equipment identity (IMEI) 674 for identifying the device 600 to other networked devices; and instructions (not shown) for any other application that may be operating on or in conjunction with the mobile computing device. Memory 650 may also store other software instructions for facilitating other processes, features and applications, such as applications related to navigation, social networking, location-based services or map displays.

Each of the above identified instructions and applications can correspond to a set of instructions for performing one or more functions described above. These instructions need not be implemented as separate software programs, procedures, or modules. Memory 650 can include additional or fewer instructions. Furthermore, various functions of the mobile device may be implemented in hardware and/or in software, including in one or more signal processing and/or application specific integrated circuits.

Certain features may be implemented in a computer system that includes a back-end component, such as a data server, that includes a middleware component, such as an application server or an Internet server, or that includes a front-end component, such as a client computer having a graphical user interface or an Internet browser, or any combination of the foregoing. The components of the system can be connected by any form or medium of digital data communication such as a communication network. Some examples of communication networks include LAN, WAN and the computers and networks forming the Internet. The computer system can include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an API that can define one or more parameters that are passed between a calling application and other software code such as an operating system, library routine, or a function that provides a service, that provides data, or that performs an operation or a computation. The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API. In some implementations, an API call can report to an application the capabilities of a device running the application, such as input capability, output capability, processing capability, power capability, and communications capability.

Figure 7:
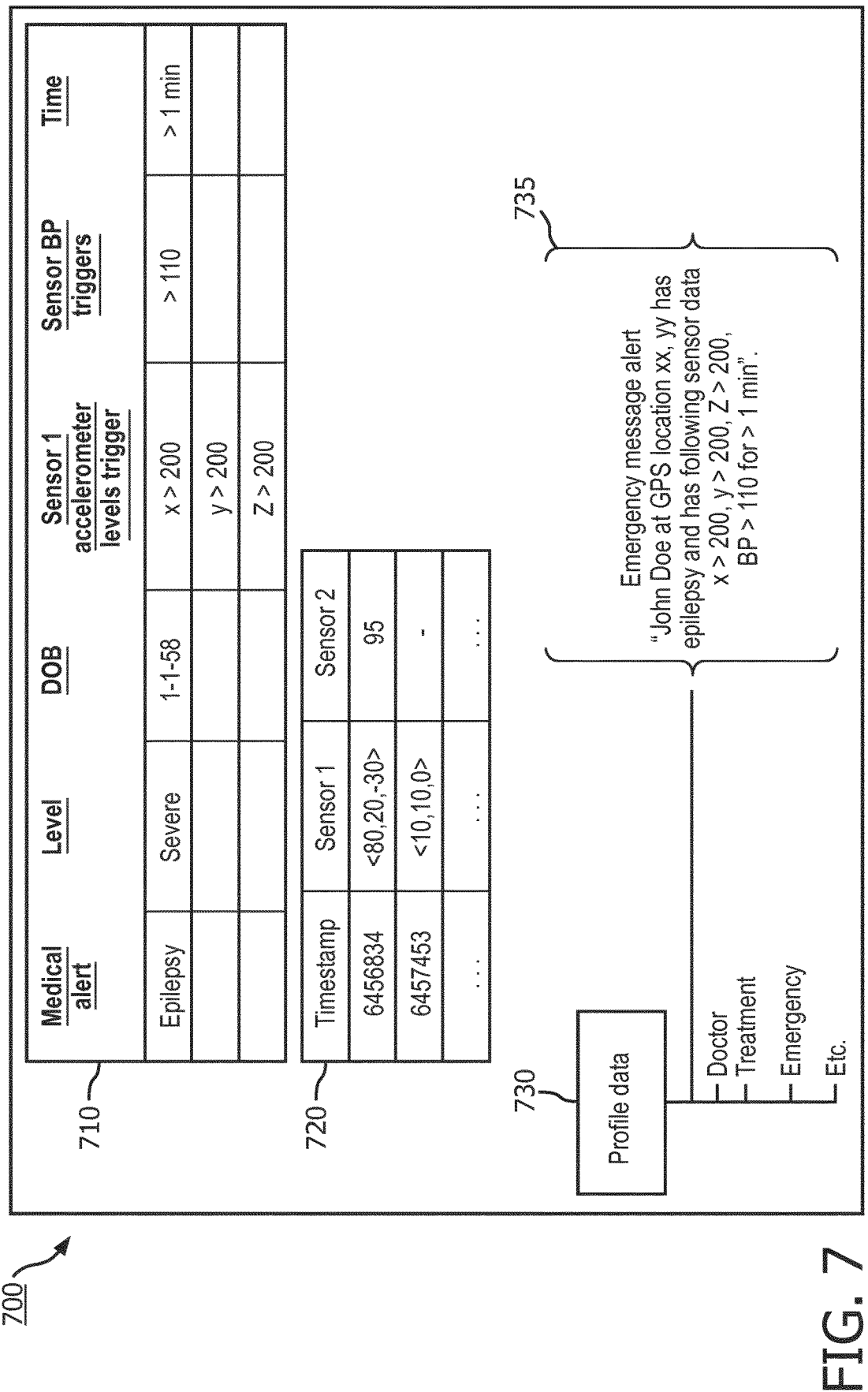
FIG. 7 illustrates an example wearable database.

FIG. 7 illustrates an example wearable database 700. The wearable database may include information such as medical alert information 710. The medical alert information 710 may include various types of medical information that are provided in existing medical bracelets (e.g., medical condition, emergency contact). Medical alert information 710 included in the wearable database may include the date of birth for the user, the level of severity of the medical condition, related sensor data used to monitor and detect the medical condition and a time frame for the measurement of sensor data taken. In various embodiments, the medical alert information 710 may additionally or alternatively define one or more triggers for identifying a medical event and prompting action by the wearable device, user device, or other device such as, for example, messaging a doctor, hospital, or emergency contact. In the example shown in FIG. 7, the medical alert information 710 indicates a trigger related to a patient's epilepsy. This example trigger will be activated with the accelerometer reads levels in all three directions above 200 and the blood pressure sensor reads blood pressure over 110 for over 1 minute duration. While not illustrated, the medial alert information 710 may, in some embodiments, further define one or more actions to be taken when a trigger is activated. In other embodiments, the appropriate action to be taken may be defined elsewhere such as, for example, a global messaging setting such as may have been input through the example GUI 300.

The wearable database may also include historic medical data 720 obtained from the wearable device. For example, the wearable database can store all the previous sensor measurements taken by the wearable device for later reference. As shown in the illustrated example, each sensor reading (or set of sensor readings taken at a single time) may be stored as a record associated with a timestamp indicating when the reading(s) was measured. Various additional or alternative history information 720 for storage will be apparent. For example, the history 720 may include indications of events such as trigger activations or emergency responses. As another example, the history 720 may include data retrieved from another source such as a physician, an electronic health record, or another wearable device.

The wearable database further includes profile data 730 corresponding to the user. The profile data 730 may include information about the medical history and contacts for the user. Such contact information of the user may include doctors and their contact information, known treatment for the medical condition, and emergency contacts to friends, family or emergency services. There may be an emergency message alert 735 that may be provided in situations where the user would like to provide a message but cannot do so (e.g., unable to speak or incapacitated). For example, upon activation of a the trigger defined by the medical alert information 710, the emergency message alert 735 may be provided with the current location of the patient and then transmitted to the doctor or emergency numbers defined in the profile data 730 or displayed on a display of the wearable device or user device.

In various embodiments, the profile data 730 may include multiple messages 735 to be transmitted as at last part of the beacon. For example, a default message may be defined for transmission at times when no defined triggers have been met while a different emergency message may be defined for transmission for each defined trigger. As shown, the message 735 may be stored as a parameterized template which, prior to broadcast as part of the beacon, will be filled out with actual data from one of more sensors or other sources. As such, keywords may be defined and recognized by the broadcasting device (e.g., wearable device or mobile device) as requiring replacement with data prior to message transmission. In the shown example message, the keywords "xx" and "yy" may be understood to refer to longitude and latitude values to be retrieved from a GPS system. It will be understood that similar keywords may be defined to refer to other current, recent, or historical data values including sensor readings, calculated parameters, other information stored in the profile data 730, or virtually any other data accessible to the wearable device or mobile device either locally or by communicating with other devices (e.g., via a packet network).

In some embodiments, the messages 735 may be provided in the wearable device or mobile device by the wearer or another user. For example, the user may access an interface provided via the wearable device 110, mobile device 120, personal computer, or web server for selecting predefined messages or for writing new messages for inclusion within the profile data. Similarly, this or other interfaces may enable the user to define other data such as identification of medical conditions, demographic information, emergency contacts, triggers, or any other data driving the operation of, or otherwise used by, the wearable device 110 or mobile device 120.

The information in the wearable database could be provided to the user mobile device during synchronization. Alternatively, the wearable database can also provide this information to third parties using mobile readers. As indicated above, the user may transmit additional information (including the information in the wearable database) upon a read of the trigger signal by a third party. The read of the trigger signal may be indicative of a request to evaluate and determine the current health condition of the user.

Figure 8A:
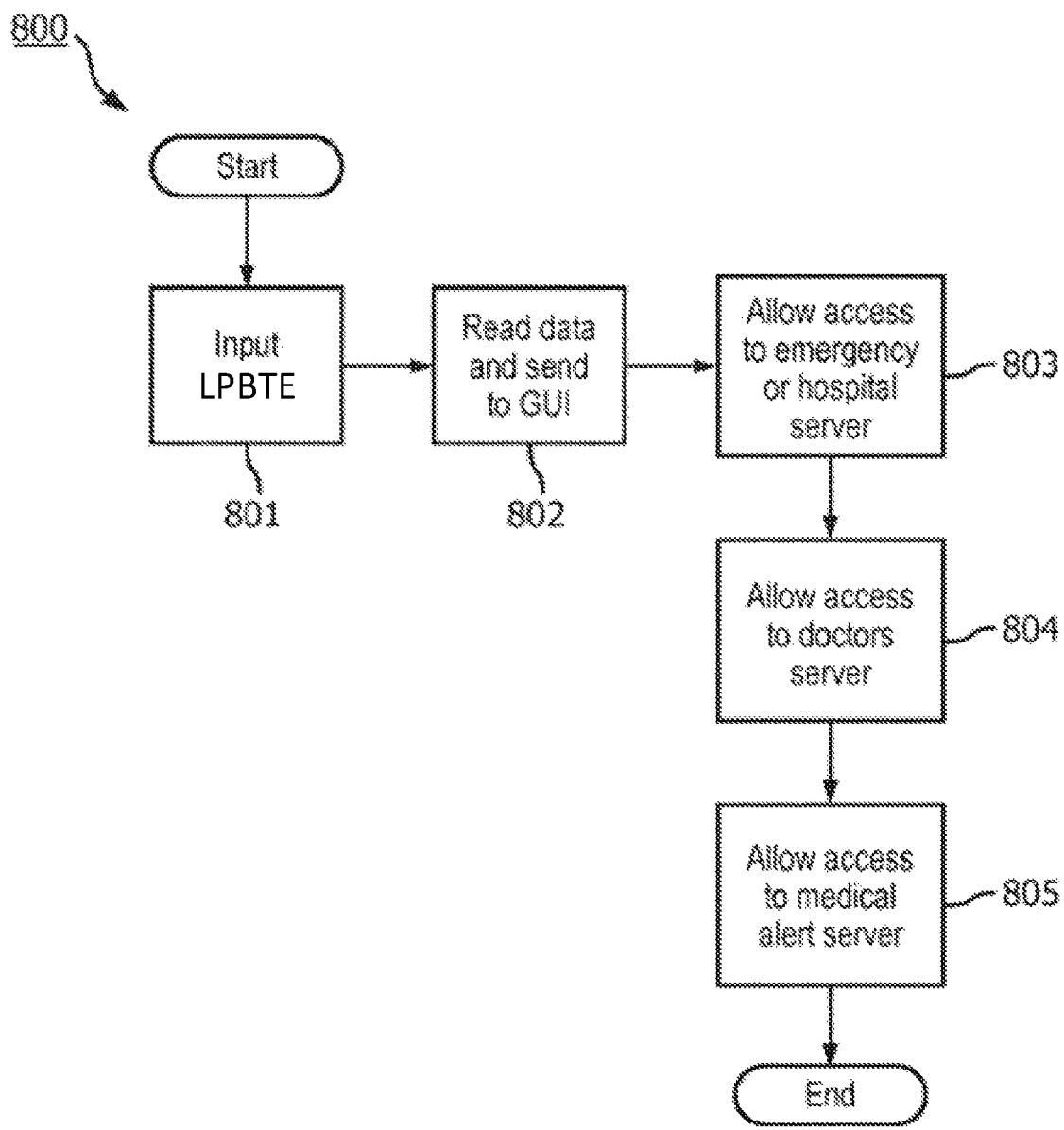
FIG. 8A illustrates example base software found in the mobile reader.

FIG. 8A illustrates example base software 800 found in the mobile reader. The base software may be responsible for the various functionalities of the mobile reader as implemented in the present invention. In various embodiments, the example base software may correspond to the reader base software 131 of FIG. 1.

In step 801, the base software of the mobile reader may take as input the information transmitted from the user mobile device or the user wearable device. The information may be provided from the trigger signal using low-powered Bluetooth communication, e.g. "Input LPBTE."

In step 802, the base software may perform a read operation on the information provided from the user (e.g., mobile device and/or wearable device). The information may then be displayed on the GUI of the mobile reader. By displaying the information on the mobile reader, the third party (e.g., first responders) using the mobile reader may be able to view the information and determine what may be necessary to provide assistance and/or treatment for the user.

Figure 8B:
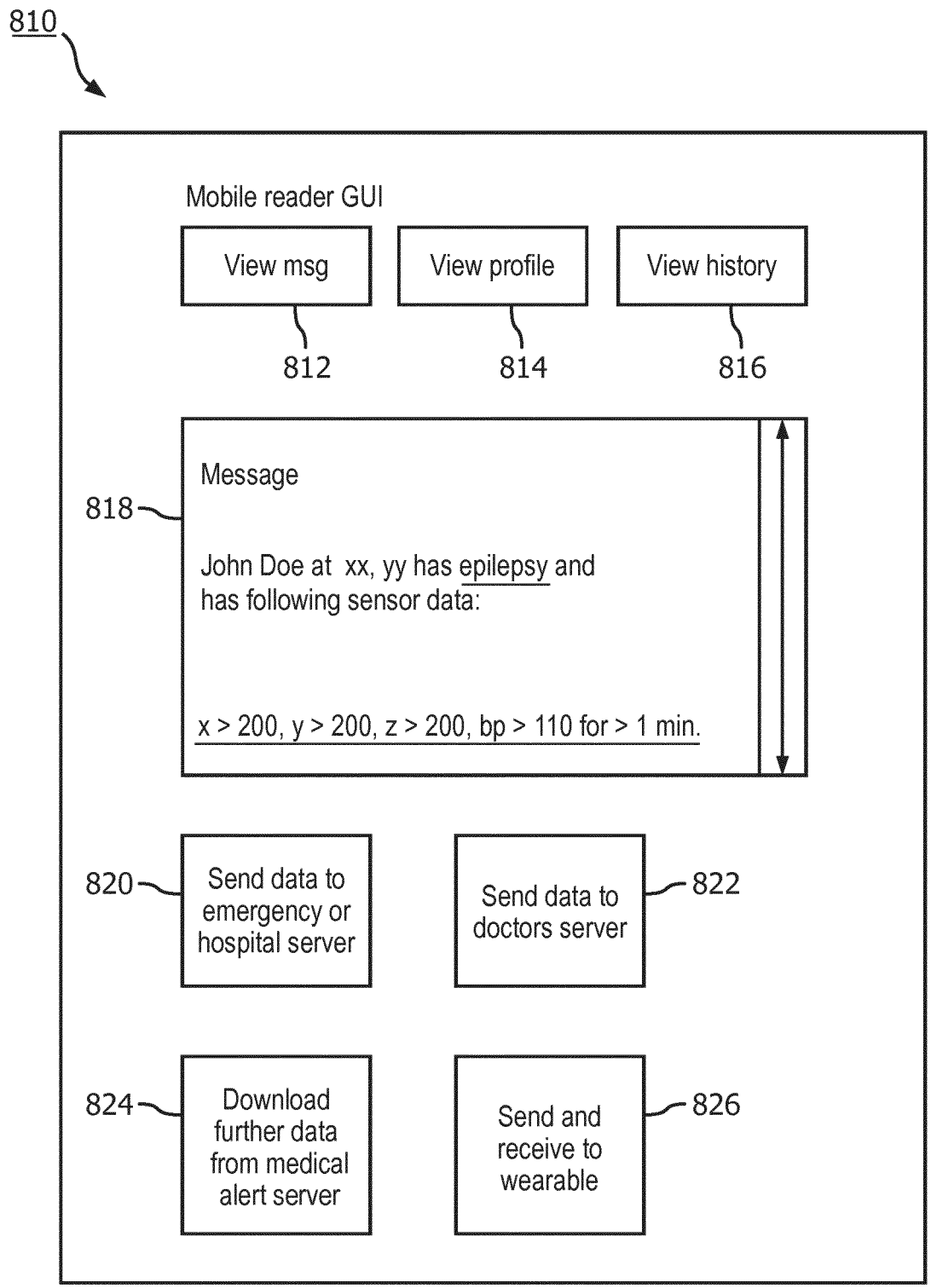
FIG. 8B illustrates an example GUI found in the mobile reader.

In steps 803, 804, 805, the mobile reader may attempt to access additional information from one or more available servers. The mobile reader may try to access additional information about the medical condition. In another embodiment, the mobile reader may attempt to request additional information about the user (e.g., medical history, user profile). Access for the mobile reader may be dependent on the authorization FIG. 8B illustrates an example GUI 810 found in the mobile reader such as, for example, the GUI 133 of the mobile reader 130 in FIG. 1. The GUI 810 may allow an individual, or entity (e.g., first responder) to view emergency messages, medical profile of the user and medical history of the user. For example, as shown, the GUI may provide a message button 812, a profile button 814, and a history button 816. Upon selection of one of these buttons 812, 814, 816, a view window 818 may be updated to display a received message, patient profile, or patient medical history, respectively. Such information may be received from, for example, a user device (e.g., a mobile device, wearable device, or other device operated by a user). In various embodiments, the displayed information may be retrieved from or supplemented by information received from another server such as, a doctors server, hospital server, etc. In the example shown, the display window 818 is displaying a received message indicating that a user has triggered an epilepsy alert such as, for example, in the manner described above with respect to FIG. 7.

The GUI 810 may also provide options for the individual or entity to provide the information in the GUI to other servers (e.g., doctors server), download further information from one or more available server (e.g., the medical alert server) or provide notice to the wearable device that receipt of the information has been completed. As shown, the GUI 810 provides a hospital server button 820 and doctors server button 822 that, upon selection, may forward the received information to the hospital or doctors server, respectively. A download button 824 may be selectable to cause the device to download any additional data about the patient that is available such as, for example, from the hospital or doctors server. Finally, a wearable button 826 may be selectable to initiate communications with the wearable device or user device. For example, selection of the wearable button 826 may open a text messaging window to enable sending and receiving text messages with the wearable device or user device.

It should be noted that the GUI 810 on the reader may be designed to display different types of information and provide many different options that are not illustrated in FIG. 8B. Goals of the GUI 810 include displaying relevant information and options to use the information in order to better facilitate treatment of the user for the detected medical condition.

Figure 9:
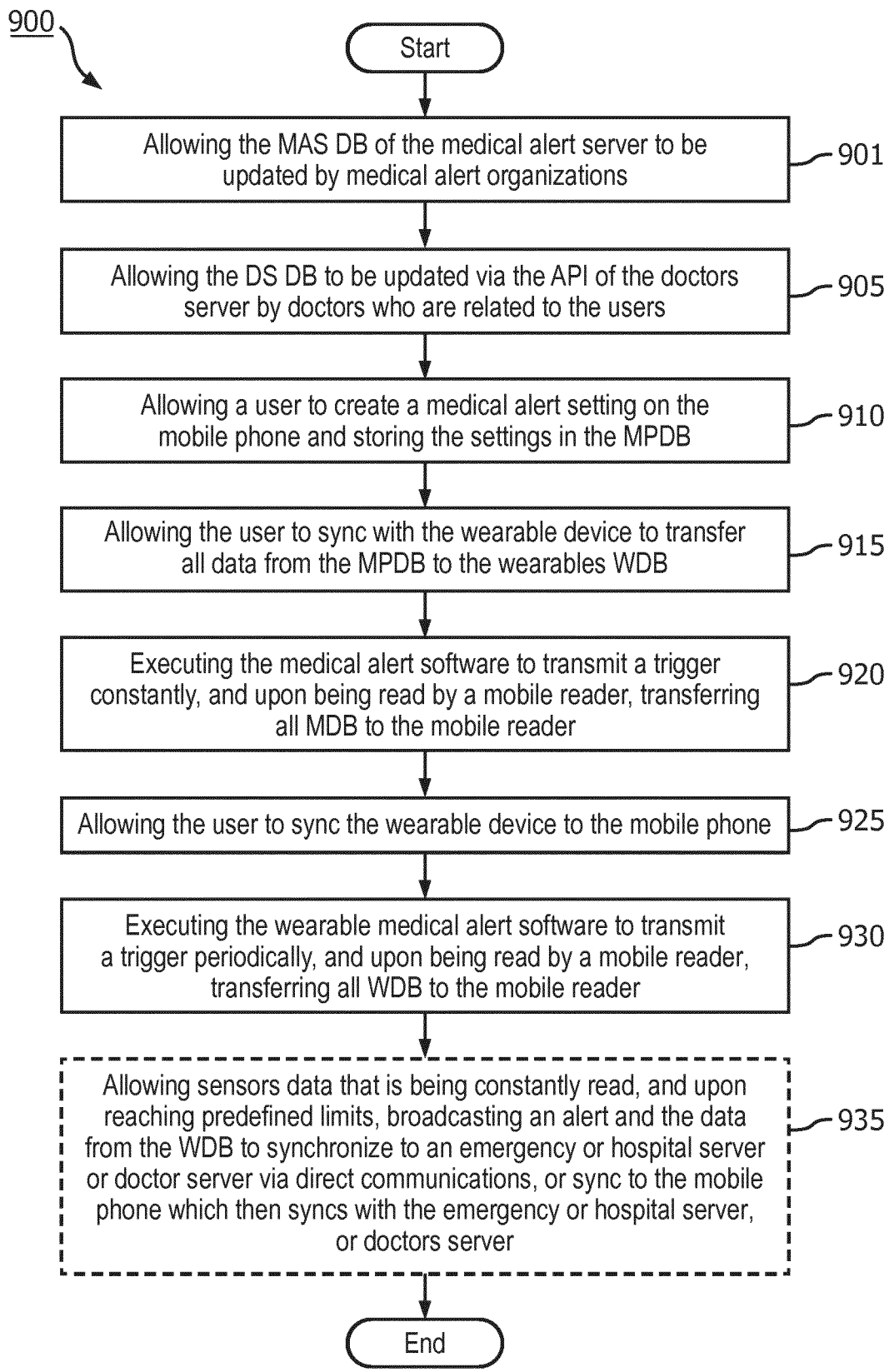
FIG. 9 illustrates an example overall method of the system as described herein.

FIG. 9 illustrates an example overall method 900 of the system as described herein. It should be noted that the steps illustrated in FIG. 9 show an embodiment. In other embodiments, different steps, additional steps, fewer steps and steps in different orders are all possible. The steps, however, are all directed at facilitating providing a health monitoring system using both the user mobile device and the wearable device.

In steps 901 and 905, databases of the various networks (e.g., the medical alert networks and doctors network) may be updated by one or more different entities. As indicated above, each of the networks may include an API where third parties may update the information stored in the database. The information updated may include information about medical conditions, emergency contacts, and user profiles.

In step 910, the user may configure the mobile device (e.g., mobile phone) for detecting one or more medical conditions. As described above in FIG. 3, the user may select one or more settings to instruct the mobile device on various features including what types of sensor data to monitor, where data should be stored, what networks can be accessed and how information (e.g., trigger sensor) is transmitted. The various settings may be stored in the database of the mobile device.

In step 915/925, the user may synchronize the information between the mobile device and the wearable device. The information provided to the wearable device may include instructions for the wearable device on what parameters the wearable device needs to monitor for a particular medical condition. For example, mobile device may instruct the wearable device to obtain temperature sensor data, blood pressure and movement data in order to monitor for the presence of asthma (see FIG. 2). Also, sensor data obtained by the wearable device may be provided to the mobile device and stored in the database of the mobile device. The stored sensor data can then be used by the mobile device to transmit related information via trigger signal to a third party for monitoring the health condition of the user.

In step 920/930, the medical alert base software of the wearable device and/or mobile device may transmit user information via a trigger signal. The trigger signal may be read by any third party (e.g., network or device). In other embodiments, the user may direct the trigger signal at a particular third party (e.g., doctor, hospital servers). The third party can then perform a read operation on the trigger signal that would indicate that the user device (e.g., wearable device and/or mobile device) to transmit additional information to the third party regarding the health condition of the user.

In step 935, the method can be directed at notifying a third party (e.g., doctor, hospital, emergency contacts) when an emergency condition has been detected. In particular, sensor data can be continually polled from the wearable device, the sensor data directed at monitoring and measuring one or more parameters related to a particular medical condition. For each parameter measured, a corresponding threshold limit may be assigned that can be used to indicate an appropriate measurement. In situations where sensor data exceeds the threshold limit, this may be indicative of an abnormal measurement and that a medical condition may have been detected.

The wearable device may continually poll sensor data. In other embodiments, the sensor data may be obtained at regular intervals. Once sensor data exceeds a defined threshold for a particular parameter, the user (via the wearable device and/or the mobile device) may then provide an alert to corresponding third parties (e.g., networks, doctors, hospitals) regarding a potential detected medical condition. Information about the medical condition may be provided to the third parties for further evaluation through an initial message. The message may include not only the monitored sensor data but also related user information. The third parties may also request additional information (e.g., medical history) from the user or other sources to determine whether the medical condition is actionable. If it is deemed actionable (in other words, the user is determined to need assistance or treatment), the third party may then initiate steps to provide the assistance or treatment to the user.

The wearable device and/or the mobile device, during this time, may communicate back and forth with the third parties providing additional information about the condition of the user and the location of the user (via GPS). In this way, the third parties may be informed of the health condition of the user (e.g., whether the user is conscious) and the user may be informed of the proximity of the third party.

According to the foregoing, various embodiments of the wearable device described herein provide a significant advantage in that medical alert information may be automatically communicated to devices of nearby people, such as emergency first responders. As such, the potential for an interested party to overlook the presence of a medical alert item on the body of (or otherwise near) the wearer is reduced or eliminated. Further, various embodiments offer the advantage that additional information, typically unavailable in existing and non-electronic medical alert items, may be automatically or on-demand transmitted to the interested party. For example, in addition to receiving static information about a patient's condition, demographics, and emergency contacts, a device of a nearby first responder may also receive dynamic information such as sensor information or information about the recent occurrence of medical events, such as seizures. As such, interested parties are provided with rapid, easy and/or automatic access to sensor and related data from a patient's wearable device. Such access is particularly valuable in medical emergency situations where time is of the essence. Additional advantages of the embodiments described herein will be apparent in view of the foregoing.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A mobile user device comprising:
a wireless communications interface configured to communicate wirelessly with nearby reader devices;
a memory; and
a processor in communication with the communications interface and the memory, wherein the processor is configured to:
receive, at a user interface of the mobile user device, a user selection identifying a medical event to be monitored for alerting third parties with respect to a user possessing the mobile user device, wherein the medical event is associated with a trigger;
receive health parameters of the user obtained by at least one sensor configured to sense one or more health parameters from the user;
identify as a medical alert the occurrence of the monitored medical event based on a comparison of the received health parameters and the trigger;
persist the medical alert in the memory;
generate an information alert that includes at least one of the medical alert and an indication of the availability of the medical alert; and
repeatedly broadcast, via the communications interface, the same information alert.

2. The user device of claim 1, wherein, in repeatedly broadcasting the same information alert, the processor is further configured to additionally transmit at least one of the health parameters with the same information alert.

3. The user device of claim 2, wherein the processor is further configured to select the at least one of the health parameters for transmission based on the identification of the medical alert.

4. The user device of claim 1, wherein, in receiving the identification of a medical event to be monitored, the processor is configured to receive a user selection of the medical alert from a list of predefined possible medical alerts.

5. A method performed by a mobile user device for providing medical alert information, the method comprising:
receiving, at a user interface of the mobile user device, a user selection identifying a medical event to be monitored for alerting third parties with respect to a user possessing the mobile user device, wherein the medical event is associated with a trigger;
receiving, by a processor of the mobile user device, health parameters of a user obtained by at least one sensor configured to sense one or more health parameters from the user;
identifying as a medical alert the occurrence of the monitored medical event based on a comparison of the received health parameters and the trigger;
persisting the medical alert in a memory of the mobile user device;
generating an information alert that includes at least one of the medical alert and an indication of the availability of the medical alert; and
repeatedly broadcasting, via a wireless communications interface, the same information alert.

6. The method of claim 5, wherein repeatedly broadcasting the same information alert comprises additionally transmitting at least one of the health parameters with the same information alert.

7. The method of claim 6, further comprising selecting the at least one of the health parameters for transmission based on the identification of the medical alert.

8. The method of claim 5, wherein, receiving the identification of a medical event to be monitored comprises receiving a user selection of the medical alert from a list of predefined possible medical alerts.

9. A non-transitory machine-readable storage medium encoded with instructions for execution by a mobile user device for providing medical alert information, the non-transitory machine-readable storage medium comprising:
instructions for receiving, at a user interface of the mobile user device, a user selection identifying a medical event to be monitored for alerting third parties with respect to a user possessing the mobile user device, wherein the medical event is associated with a trigger;
instructions for receiving, by a processor of the mobile user device, health parameters of the user obtained by at least one sensor configured to sense one or more health parameters from the user;
instructions for identifying as a medical alert the occurrence of the monitored medical event based on a comparison of the received health parameters and the trigger;
instructions for persisting the medical alert in a memory of the mobile user device;
instructions for generating an information alert that includes at least one of the medical alert and an indication of the availability of the medical alert; and
instructions for repeatedly broadcasting, via a wireless communications interface, the same information alert.

10. The non-transitory machine-readable storage medium of claim 9, wherein repeatedly broadcasting the same information alert includes additionally transmitting at least one of the health parameters with the same information alert.

11. The non-transitory machine-readable storage medium of claim 10, further comprising instructions to select the at least one of the health parameters for transmission based on the identification of the medical alert.

12. The non-transitory machine-readable storage medium of claim 10, wherein receiving the identification of a medical event to be monitored includes receiving a user selection of the medical event to be monitored from a list of predefined possible medical alerts.

* * * * *